(12) United States Patent
Masuno et al.

(10) Patent No.: US 10,392,317 B2
(45) Date of Patent: Aug. 27, 2019

(54) METHODS OF PRODUCING PARA-XYLENE AND TEREPHTHALIC ACID

(71) Applicant: MICROMIDAS, INC., West Sacramento, CA (US)

(72) Inventors: Makoto N. Masuno, Elk Grove, CA (US); Ryan L. Smith, Sacramento, CA (US); John Bissell, II, Sacramento, CA (US); Patrick B. Smith, Midland, MI (US); Dennis A. Hucul, Midland, MI (US); Edmund J. Stark, Midland, MI (US); Daniel R. Henton, Midland, MI (US); Adina Dumitrascu, Midland, MI (US); Katherine Brune, Midland, MI (US); Dimitri A. Hirsch-Weil, West Sacramento, CA (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 14/428,339

(22) PCT Filed: Sep. 13, 2013

(86) PCT No.: PCT/US2013/059660
§ 371 (c)(1),
(2) Date: Mar. 13, 2015

(87) PCT Pub. No.: WO2014/043468
PCT Pub. Date: Mar. 20, 2014

(65) Prior Publication Data
US 2015/0266793 A1 Sep. 24, 2015

Related U.S. Application Data

(63) Continuation-in-part of application No. 13/838,761, filed on Mar. 15, 2013, now Pat. No. 8,889,938.

(60) Provisional application No. 61/701,276, filed on Sep. 14, 2012.

(51) Int. Cl.
*C07C 6/04* (2006.01)
*C07C 2/86* (2006.01)

(52) U.S. Cl.
CPC ............... *C07C 2/867* (2013.01); *C07C 6/04* (2013.01); *C07C 2521/04* (2013.01); *C07C 2521/18* (2013.01); *C07C 2523/08* (2013.01); *C07C 2523/10* (2013.01); *C07C 2523/72* (2013.01); *C07C 2527/122* (2013.01); *C07C 2527/125* (2013.01); *C07C 2527/126* (2013.01); *C07C 2527/128* (2013.01); *C07C 2527/133* (2013.01); *C07C 2527/135* (2013.01); *C07C 2527/138* (2013.01); *C07C 2527/18* (2013.01); *C07C 2527/19* (2013.01); *C07C 2529/14* (2013.01); *C07C 2529/24* (2013.01); *C07C 2531/025* (2013.01); *C07C 2531/04* (2013.01); *C07C 2531/22* (2013.01)

(58) Field of Classification Search
None
See application file for complete search history.

(56) References Cited

U.S. PATENT DOCUMENTS

| | | | |
|---|---|---|---|
| 2,781,407 | A | 2/1957 | Schmerling |
| 3,819,714 | A | 6/1974 | Bluestone et al. |
| 3,947,521 | A | 3/1976 | Lasco |
| 4,335,049 | A | 6/1982 | Hamada et al. |
| 7,060,862 | B2 | 6/2006 | Jong et al. |
| 7,385,081 | B1 | 6/2008 | Gong |
| 7,608,727 | B2 | 10/2009 | Ishii et al. |
| 7,790,431 | B2 | 9/2010 | Frost |
| 8,314,267 | B2 | 11/2012 | Brandvold |
| 8,889,938 | B2 | 11/2014 | Masuno et al. |
| 8,933,281 | B2 | 1/2015 | Cortright et al. |
| 8,962,902 | B2 | 2/2015 | Blommel et al. |
| 8,969,640 | B2 | 3/2015 | Blommel et al. |
| 9,260,359 | B2 | 2/2016 | Masuno et al. |
| 9,890,101 | B2 | 2/2018 | Masuno et al. |
| 10,125,060 | B2 | 11/2018 | Masuno et al. |
| 2010/0331568 | A1 | 12/2010 | Brandvold |
| 2012/0029257 | A1 | 2/2012 | Chen et al. |
| 2013/0245316 | A1 | 9/2013 | Masuno et al. |
| 2014/0273118 | A1 | 9/2014 | Held et al. |
| 2014/0275571 | A1 | 9/2014 | Beck et al. |
| 2014/0296600 | A1 | 10/2014 | Dauenhauer et al. |
| 2014/0349361 | A1 | 11/2014 | Blommel et al. |
| 2014/0350294 | A1 | 11/2014 | Masuno et al. |

(Continued)

FOREIGN PATENT DOCUMENTS

| | | |
|---|---|---|
| CN | 101116828 A | 2/2008 |
| CN | 102050687 A | 5/2011 |

(Continued)

OTHER PUBLICATIONS

Reymond et al. Chem. Rev. 2008, 108, 5359-5406.*

(Continued)

*Primary Examiner* — Ana Z Muresan
(74) *Attorney, Agent, or Firm* — Morrison & Foerster LLP

(57) ABSTRACT

The present disclosure provides methods to produce para-xylene, toluene, and other compounds from renewable sources (e.g., cellulose, hemicellulose, starch, sugar) and ethylene in the presence of a catalyst. For example, cellulose and/or hemicellulose may be converted into 2,5-dimethylfuran (DMF), which may be converted into para-xylene by cycloaddition of ethylene to DMF. Para-xylene can then be oxidized to form terephthalic acid.

28 Claims, No Drawings

(56) References Cited

U.S. PATENT DOCUMENTS

| | | |
|---|---|---|
| 2014/0350317 A1 | 11/2014 | Blommel et al. |
| 2015/0020797 A1 | 1/2015 | Eyal et al. |
| 2015/0028255 A1 | 1/2015 | Eyal et al. |
| 2015/0048274 A1 | 2/2015 | Eyal et al. |
| 2015/0141667 A1 | 5/2015 | Blank et al. |
| 2015/0141695 A1 | 5/2015 | Masuno et al. |
| 2016/0362357 A1 | 12/2016 | Masuno et al. |
| 2016/0368837 A1 | 12/2016 | Masuno et al. |

FOREIGN PATENT DOCUMENTS

| | | |
|---|---|---|
| CN | 102482177 A | 5/2012 |
| EP | 2061860 A1 | 5/2009 |
| FR | 2551071 A1 | 3/1985 |
| JP | 2000-136304 A | 5/2000 |
| JP | 2000-169425 A | 6/2000 |
| JP | 2003-055280 A2 | 2/2003 |
| JP | 2003-104916 A | 4/2003 |
| JP | 2004-168831 A | 6/2004 |
| JP | 2004-244579 A | 9/2004 |
| JP | 2009-242251 A | 10/2009 |
| JP | 2011-116709 A2 | 12/2009 |
| SU | 844617 | 7/1981 |
| WO | 2008/109877 A1 | 9/2008 |
| WO | 2009/110402 A1 | 9/2009 |
| WO | 2010/148049 A2 | 12/2010 |
| WO | 2010/151346 A1 | 12/2010 |
| WO | 2010148081 A2 | 12/2010 |
| WO | 2012/061272 A2 | 5/2012 |
| WO | 2012/092436 A1 | 7/2012 |
| WO | 2013/040514 A1 | 3/2013 |
| WO | 2014/043468 A1 | 3/2014 |
| WO | 2014/065657 A1 | 5/2014 |
| WO | 2014/152370 A2 | 9/2014 |
| WO | 2014/190124 A1 | 11/2014 |
| WO | 2014/190161 A1 | 11/2014 |

OTHER PUBLICATIONS

Nie et al. Catalysis Today 36 (1997) 81-84.*
Cheng, Yu-Ting, "Catalytic Fast Pyrolysis of Furan Over ZSM-5 Catalysts: A Model Biomass Conversion Reaction", Chemical Engineering, Sep. 2012, 165 pages.
Cheng et al., "Production of Targeted Aromatics by using Diels—Alder Classes of Reactions with Furans and Olefins over ZSM-5", Green Chemistry, vol. 14 No. 11, Oct. 2012, pp. 3114-3125.
Non-Final Office Action received for U.S. Appl. No. 14/519,034, dated Jul. 22, 2015, 9 pages.
Notice of Allowance received for U.S. Appl. No. 14/345,216, dated Oct. 6, 2015, 9 pages.
International Preliminary Report on Patentability received for PCT Patent Application No. PCT/US2013/59660 dated Mar. 26, 2015, 9 pages.
International Search Report and Written Opinion received for PCT Patent Application No. PCT/US2013/059660. dated Nov. 25, 2013, 14 pages.
International Search Report and Written Opinion received for PCT Patent Application No. PCT/US2012/055651. dated Dec. 19, 2012, 8 pages.
International Preliminary Report on Patentability received for PCT Patent Application No. PCT/US2012/055651, dated Mar. 27, 2014, 6 pages.
Non Final Office Action received for U.S. Appl. No. 13/838,761, dated Jan. 16, 2014, 6 pages.
Notice of Allowance received for U.S. Appl. No. 13/838,761, dated Jul. 21, 2014, 9 pages.
Dauenhauer et al., "Renewable Catalytic Process for the Production of P-Xylene", Abstracts of Papers, 246th ACS National Meeting & Exposition, Indianapolis, Sep. 8-12, 2013, 1 page.
Hanamoto et al., "Palladium-Catalyzed Carbonylative Coupling of Tributyi(1-Ftuorovinyl)stannane with Aryl Halides and Aryl Triftates", Bulletin of the Chemical Society of Japan, vol. 75, No. 11, 2002, pp. 2497-2502.

Kandil et al., "The Synthesis and Characterization of New Schiff Bases and Investigating them in Solvent Extraction of Chromium and Copper", Separation Science and Technology, vol. 47, 2012, pp. 17541761.
Li et al., "Production and Separation of Phenols from Biomass-Derived Bio-Petroleum", Journal of Analytical and Applied Pyrolysis, vol. 89, 2010, pp. 218-224.
Robbins et al., "A C—H Borylation Approach to Suzuki-Miyaura Coupling of Typically Unstable 2-Heteroaryl and Polyfluorophenyl Boronates", Organic Letters, vol. 14, No. 16, 2012, pp. 4266-4269.
Wahyudiono et al., "Supercritical Water as a Reaction Medium for Nitrogen-Containing Heterocycles", Journal of Chemistry and Chemical Engineering, vol. 6, 2012, pp. 897-910.
Wang et al., "Selective Production of Aromatics from Alkylfurans over Solid Acid Catalysts", ChemCatChem, vol. 5, 2013, pp. 2044-2050.
Xu et al., "A Novel Cis-Chelated Pd(II)-NHC Complex for Catalyzing Suzuki and Heck-Type Cross-Coupling Reactions", Tetrahedron, vol. 61, 2005, pp. 11225-11229.
Antoniotti et al., "Metal Triflimidates: Better than Metal Triftates as Catalysts in Organic Synthesis—The Effect of a Highly Delocalized Counteranion", Angewandte Chemie International Edition, vol. 49, No. 43, Oct. 18, 2010, pp. 7860-7888.
Baldwin et al., "Rearrangements of Toluene and Cycloheptatriene Cations", J. Am. Chem. Soc., vol. 97, No. 21, 1975, pp. 6169-6174.
Brasholz et al., "Highly Efficient Dehydration of Carbohydrates to 5-(chloromethyi)Furfurai(CMF), 5-(hydroxymethyl)Furfural (HMF) and Levulinic acid by Biphasic Continuous Flow Processing", Green Chemistry, vol. 13, 2011, pp. 1114-1117.
Chang et al., "Ultra-Selective Cycloaddition of Dimethylfuran for Renewable P-Xylene with H-BEA", Green Chemistry, The Royal Society of Chemistry, 2013, 4 pages.
Deutsch et al., "Active Species of Copper Chromite Catalyst in C-0 Hydrogenolysis of 5-Methylfurfuryl Alcohol", Journal of Catalysis, vol. 285, No. 1, Jan. 2012, pp. 235-241.
Hayashi et al., "The HfCl4-Mediated Diels-Aider Reaction of Furan", Angewandte Chemie International Edition, vol. 41, No. 21, 2002, pp. 4079-4082.
Jarzecki et al., "Thermal Rearrangements of Norcaradiene", J. Am. Chem. Soc., vol. 121, No. 29, 1999, pp. 6928-6935.
Kobayashi et al., "Rare-Earth Metal Triflates in Organic Synthesis", Chemical Reviews, vol. 102, No. 6, 2002, pp. 2227-2302.
Lessard et al.. "High Yield Conversion of Residual Pentoses into Furfural via Zeolite Catalysis and Catalytic Hydrogenation of Furfural to 2-Methylfuran". Topics in Catalysis. vol. 53. No. 15-18, Sep. 2010, pp. 1231-1234.
Lin et al., "Aromatics from Lignocellulosic Biomass: Economic Analysis of the Production of p-Xylene from 5-Hydroxymethylfurfural", AIChE Journal, vol. 59, No. 6, Jun. 2013, pp. 2079-2087.
Moore et al., "Catalyzed Addition of Furan with Acrylic Monomers", J. Org. Chern., vol. 48, No. 7, 1983, pp. 1105-1106.
Nikbin et al., "A OFT Study of the Acid-Catalyzed Conversion of 2,5-Dimethylfuran and Ethylene to P-Xylene", Journal of Catalysis, vol. 297, 2013, pp. 35-43.
Otto et al., "Diels-Aider Reactions in Water", Pure Appl. Chern., vol. 72, No. 7, 2000, pp. 1365-1372.
Otto, Sijbren, "Catalysis of Diels-Aider Reactions in Water", Rijksuniversiteit Groningen, Aug. 3, 1971, 203 pages.
Padwa et al., "Diels-Aider Reaction of 2-Amino-Substituted Furans as a Method for Preparing Substituted Anilines", J. Org. Chern., vol. 62, No. 12, 1997, pp. 4088-4096.
Prakash et al., "Gallium(III) Triftate: An Efficient and a Sustainable Lewis Acid Catalyst for Organic Synthetic Transformations", Ace. Chern. Res., vol. 45, No. 4, 2012, pp. 565-577.
Rylander, Paul N., "Catalytic Hydrogenation Over Platinum Metals", Academic Press Inc. 111 Fifth Avenue, New York, NY 10003, Jun. 1967, 565 pages.
Shiramizu et al., "On the Diels-Aider Approach to Solely Biomass-Derived Polyethylene Terephthalate (PET): Conversion of 2,5-Dimethylfuran and Acrolein into p-xylene", Chemistry A European Journal, vol. 17, 2011, pp. 12452-12457.

(56) References Cited

OTHER PUBLICATIONS

Wong et al., "Arene Syntheses by Dehydration of 7-0xabicyclo[2.2.1]heptene Systems", Heterocycles, vol. 22, No. 4, 1984, pp. 875-890.

Bautista et al., "Acetonylacetone Conversion on AlPO4-Cesium Oxide (5-30 wl%) Catalysts", Catalysis Letters, vol. 60, 1999, pp. 145-149.

Do et al., "Elucidation of Diels-Aider Reaction Network of 2,5-Dimethylfuran and Ethylene on HY Zeolite Catalyst", ACS Catalysis, vol. 3, 2013, pp. 41-46.

Farina et al., "The Stille Reaction", Organic Reactions, Chapter 1, vol. 50, 1997, 93 pages.

Fraile et al., "ZnCl2, Zn12, and TiCl4 Supported on Silica Gel as Catalysts for the Diels-Aider Reactions of Furan", Journal of Molecular Catalysis A: Chemical, vol. 123, 1997, pp. 43-47.

Hashimoto et al., "Measurement of Br0ensted Acid and Lewis Acid Strength Distributions of Solid Acid Catalysts using Chemisorption Isotherms of Hammett Indicators", Ind. Eng. Chern. Res., vol. 27, No. 10, 1988, pp. 1792-1797.

Kobayashi et al., "Development of Novel Lewis Acid Catalysts for Selective Organic Reactions in Aqueous Media", Accounts of Chemical Research, vol. 35, No. 4, 2002, pp. 209-217.

Kobayashi et al., "Lewis Acid Catalysts Stable in Water. Correlation between Catalytic Activity in Water and Hydrolysis Constants and Exchange Rate Constants for Substitution of Inner-Sphere Water Ligands", J. Am. Chern. Soc., vol. 120, No. 32, 1998, pp. 8287-8288.

McClure et al., "Diels-Aider Reactivity of a Ketovinylphosphonate with Cyclopentadiene and Furan", Tetrahedron Letters, vol. 37, No. 13, 1996, pp. 2149-2152.

Papadogianakis et al., "Catalytic Conversions in Water: A Novel Carbonylation Reaction Catalysed by Palladium Trisulfonated Triphenylphosphine Complexes", J. Chern. Soc., Chern. Commun., 1994, pp. 2659-2660.

Rebacz, Natalie A., "Hydration and Hydrolysis with Water Tolerant Lewis Acid Catalysis in High Temperature Water", A Dissertation Submitted in Partial Fulfillment of the Requirements for the Degree of Doctor of Philosophy (Chemical Engineering) in The University of Michigan, 2011, 164 pages.

Ruttink et al., "Complexation of Divalent Metal Ions with Dials in the Presence of Anion Auxiliary Ligands: Zinc-Induced Oxidation of Ethylene Glycol to Glycolaldehyde by Consecutive Hydride Ion and Proton Shifts", J. Mass. Spectrom., vol. 47, 2012, pp. 869-874.

Schwarz et al., "Methods for Preparation of Catalytic Materials", Chern. Rev., vol. 95, No. 3, 1995, pp. 477-510.

Spillman et al., "Formation and Degradation of Furfuryl Alcohol, 5-Methylfurfuryl Alcohol, Vanillyl Alcohol, and Their Ethyl Ethers in Barrel-Aged Wines", J. Agric. Food Chern, vol. 46, No. 2, 1998, pp. 657-663.

Williams et al., "Cycloaddition of Biomass-Derived Furans for Catalytic Production of Renewable p-Xylene", ACS Catalysis, vol. 2, 2012, pp. 935-939.

Chidambaram et al., "A Two-Step Approach for the Catalytic Conversion of Glucose to 2,5-Dimethylfuran in Ionic Liquids", Green Chemistry, vol. 12, 2010, pp. 1253-1262.

Non-Final Office Action received for U.S. Appl. No. 15/003,613, dated Oct. 7, 2016, 11 pages.

Final Office Action received for U.S. Appl. No. 15/003,613, dated Jul. 6, 2017, 9 pages.

Notice of Allowance received for U.S. Appl. No. 14/993,833, dated Oct. 3, 2017, 9 pages.

Notice of Allowance received for U.S. Appl. No. 15/003,613, dated Jun. 13, 2018, 8 pages.

Notice of Allowance received for U.S. Appl. No. 14/993,833, dated Jun. 1, 2017, 9 pages.

\* cited by examiner

METHODS OF PRODUCING PARA-XYLENE AND TEREPHTHALIC ACID

CROSS-REFERENCE TO RELATED APPLICATIONS

This application is a U.S. national stage application of PCT/US2013/059660, filed internationally on Sep. 13, 2013, which claims priority to U.S. Provisional Patent Application No. 61/701,276, filed Sep. 14, 2012, and which is also a continuation-in-part of U.S. patent application Ser. No. 13/838,761, filed Mar. 15, 2013 (now issued as U.S. Pat. No. 8,889,938), which claims priority to U.S. Provisional Patent Application No. 61/701,276, which are all incorporated herein by reference in their entireties.

FIELD

The present disclosure relates generally to the production of para-xylene and terephthalic acid, and more specifically to the production of para-xylene and terephthalic acid from renewable biomass resources (e.g., cellulose, hemicellulose, starch, sugar) and ethylene.

BACKGROUND

There exists a high demand to produce para-xylene and terephthalic acid from renewable biomass resources for use in the manufacture of clothing and plastics. Terephthalic acid is a precursor of polyethylene terephthalate (PET), which may be used to manufacture polyester fabrics. Terephthalic acid can be produced by oxidation of para-xylene.

Xylene is an aromatic hydrocarbon that occurs naturally in petroleum and coal tar. Commercial production of para-xylene is typically accomplished by catalyic reforming of petroleum derivatives. See e.g., U.S. Patent Application No. 2012/0029257. However, the use of petroleum-based feedstocks to commercially produce para-xylene (and hence terephthalic acid) generates greenhouse gas emissions and perpetuates reliance on petroleum resources.

Alternative methods to produce para-xylene from renewable biomass resources have been under investigation. Biomass containing cellulose and/or hemicellulose can be converted into DMF, and then DMF may be converted into para-xylene by Diels-Alder cycloaddition of ethylene. See e.g., U.S. Pat. No. 8,314,267; WO 2009/110402. The Diels-Alder conditions currently known in the art to produce para-xylene from cycloaddition of ethylene to DMF typically results in at least a portion of the DMF being converted into 2,5-hexanedione (HD), which generally polymerizes. Such a side reaction involving HD leads to a reduction of the selectivity to para-xylene. See e.g., Williams et al., *ACS Catal.* 2012, 2, 935-939; Do et al., *ACS Catal.* 2013, 3, 41-46.

Thus, what is needed in the art are alternative methods to produce para-xylene and terephthalic acid.

BRIEF SUMMARY

The present disclosure addresses this need by providing methods using particular catalysts, solvents, and reaction conditions to produce para-xylene from 2,5-dimethylfuran, 2,5-hexanedione, or a combination thereof. The para-xylene produced can then be oxidized to produce terephthalic acid.

In one aspect, provided is a method for producing one or more compounds of formula I:

wherein each $R^1$ and $R^2$ is independently hydrogen, alkyl, cycloalkyl, heterocycloalkyl, aryl, or heteroaryl, by:

a) combining one or more compounds of formula A, one or more compounds of formula B:

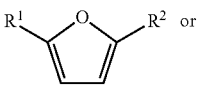

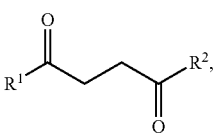

or any combinations thereof, with ethylene, a catalyst, and optionally a solvent to form a reaction mixture; and b) producing one or more compounds of formula I from at least a portion of the one or more compounds of formula A, the one or more compounds of formula B, or any combinations thereof, and at least a portion of the ethylene in the reaction mixture.

Provided is a method for producing para-xylene (i.e., where $R^1$ and $R^2$ are each methyl in formula I), by:

a) combining 2,5-dimethylfuran (DMF), 2,5-hexanedione (HD), or a combination thereof with ethylene, a catalyst, and optionally a solvent to form a reaction mixture; and b) producing para-xylene from at least a portion of the DMF, HD, or a combination thereof, and at least a portion of the ethylene in the reaction mixture.

Provided is also method for producing para-xylene (i.e., where $R^1$ and $R^2$ are each methyl in formula I), toluene (i.e., where $R^1$ is methyl and $R^2$ is hydrogen in formula I), or a combination thereof, by:

a) combining 2,5-dimethylfuran, 2-methylfuran, 2,5-hexanedione, 4-oxopentanal, or any combinations thereof with ethylene, a catalyst, and optionally a solvent to form a reaction mixture; and b) producing para-xylene from at least a portion of the 2,5-dimethylfuran, 2-methylfuran, 2,5-hexanedione, 4-oxopentanal, or a combination thereof, and at least a portion of the ethylene in the reaction mixture.

In one variation, provided is a method for producing para-xylene (i.e., where $R^1$ and $R^2$ are each methyl in formula I), by:

a) providing a starting material, wherein the starting material is 2,5-dimethylfuran (DMF), 2,5-hexanedione (HD), or a combination thereof;
b) providing ethylene;
c) providing a catalyst;
d) optionally providing a solvent;
e) combining the starting material with the ethylene, the catalyst, and optionally the solvent to form a reaction mixture; and f) producing para-xylene from at least a portion of the DMF, HD, or a combination thereof in the reaction mixture.

In another variation, provided is a method for producing para-xylene (i.e., where $R^1$ and $R^2$ are each methyl in formula I), by:
a) providing 2,5-dimethylfuran (DMF);
b) providing ethylene;
c) providing a catalyst;
d) providing a solvent;
e) combining the DMF with the ethylene, the catalyst, and the solvent to form a reaction mixture; and
f) producing para-xylene from at least a portion of the DMF in the reaction mixture.

In yet another variation, provided is a method for producing para-xylene (i.e., where $R^1$ and $R^2$ are each methyl in formula I), by:
a) providing 2,5-hexanedione (HD);
b) providing ethylene;
c) providing a catalyst;
d) optionally providing a solvent;
e) combining the HD with the ethylene, the catalyst, and optionally the solvent to form a reaction mixture; and
f) producing para-xylene from at least a portion of the HD in the reaction mixture.

In some embodiments of any of the methods described above, the method further includes isolating para-xylene from the reaction mixture.

In some embodiments of any of the methods described above, the catalyst is a metal-containing catalyst. The catalyst may include a metal cation and counterion(s). The metal cation may be selected from, for example, Group 3, Group 9, Group 10, Group 11, or the lanthanide series. In certain embodiments, the catalyst includes a monovalent metal cation, a divalent metal cation or a trivalent metal cation. The monovalent metal cation may be, for example, $Cu^+$. The divalent metal cation may be, for example, $Cu^{2+}$, $Co^{2+}$, $Cr^{3+}$, $Ni^{2+}$, $Mg^{2+}$, or $Zn^{2+}$. The trivalent metal cation may be, for example, $Al^{3+}$, $Bi^{3+}$, $Fe^{3+}$, $Gd^{3+}$, $In^{3+}$, $Nd^{3+}$, $La^{3+}$, $Sc^{3+}$, or $Y^{3+}$. Suitable counterion(s) in the catalyst may include, for example, halides (e.g., chloride, bromide), triflates (—OTf), and carboxylates (e.g. formate, acetate, acetylacetonate).

In some embodiments, the catalyst is aluminum chloride, aluminum bromide, aluminum triflate, bismuth chloride, bismuth bromide, bismuth triflate, copper chloride, copper bromide, copper triflate, copper (II) bis(trifluoromethylsulfonyl)imide, cobalt chloride, cobalt bromide, cobalt triflate, chromium chloride, chromium bromide, chromium triflate, iron chloride, iron bromide, iron triflate, gadolinium chloride, gadolinium bromide, gadolinium triflate, indium chloride, indium bromide, indium triflate, nickel chloride, nickel bromide, nickel triflate, neodymium chloride, neodymium bromide, neodymium triflate, magnesium chloride, magnesium bromide, magnesium triflate, lanthanum chloride, lanthanum bromide, lanthanum triflate, scandium chloride, scandium bromide, scandium triflate, tin chloride, tin bromide, tin triflate, titanium chloride, titanium bromide, titanium triflate, vanadium chloride, vanadium bromide, vanadium triflate, yttrium chloride, yttrium bromide, yttrium triflate, zinc chloride, zinc bromide, zinc triflate, or any combinations thereof. In one embodiment, the catalyst is copper chloride, copper triflate, or yttrium triflate.

In certain embodiments, the catalyst is $Al(OTf)_3$, $Bi(OTf)_3$, $Cu(OTf)_2$, $Cu(OTf)$, $Cr(OTf)_3$, $Fe(OTf)_3$, $Gd(OTf)_3$, $In(OTf)_3$, $Ni(OTf)_2$, $Nd(OTf)_3$, $Rb(OTf)$, $Cs(OTf)$, $Mg(OTf)_2$, $La(OTf)_3$, $Sc(OTf)_3$, $Ti(OTf)_4$, $V(OTf)_5$, $Y(OTf)_3$, $Zn(OTf)_2$, $Pt(OTf)_2$, $Pd(OTf)_2$, $AgOTf$, $Au(OTf)_3$, $Tl(OTO_3)$, $Tl(OTf)$, $Re(OTf)_3$, $Hg_2(OTf)_2$, $Hg(OTf)_2$, $NH_4(OTf)$, $Sn(OTf)_4$, $Sn(OTf)_3$, $Sn(OTf)_2$, $B(OTf)_3$, $Ga(OTf)_3$, $Pb(OTf)_4$, $Pb(OTf)_2$, $Co(OTf)_3$, $Co(OTf)_2$, $Ge(OTf)_4$, $Ge(OTf)_3$, $Ge(OTf)_2$, $Ge(OTf)$, $Ce(OTf)_4$, $Ce(OTf)_3$, or any combinations thereof.

The catalyst may be a metal salt, including any such salts that may convert in situ into a different catalytic species for the reactions described herein. For example, the catalyst used may be copper triflate. Without wishing to be bound by any theory, under certain reaction conditions, the copper triflate may yield triflic acid, which may contribute at least in part to the increase in rate of the chemical reaction.

In certain embodiments, the catalyst is unsupported. In other embodiments, the catalyst is solid supported. For example, one or more of the metal cations described above may be deposited on a solid support. Suitable supports include, for example, silica, alumina, mordenite, carbon (including, for example, activated carbon), and zeolites. In one embodiment, the catalyst may be copper (II) on mordenite, copper chloride on alumina, or copper chloride on HY zeolite. Such solid supported catalysts can more easily be recovered, recycled, and used in a continuous process.

In yet other embodiments, the catalyst may be an acid, including a Lewis acid or a weak acid. In yet other embodiments, the catalyst is a heteropolyacid. For example, in one embodiment, the catalyst is molybdosilicic acid or molybdophosphoric acid.

In yet other embodiments, the catalyst may be (a) a sulfonic acid, or a salt, ester, anhydride or resin thereof, (b) a sulfonamide, or a salt thereof, or (c) a sulfonimide, or a salt thereof. Suitable examples of such catalyst may include trifluoromethanesulfonic acid (also referred to as triflic acid), 4-methylbenzenesulfonic acid (also referred to as p-toluene-sulfonic acid), and triflimide.

In some embodiments of any of the methods described above, the solvent system includes an aprotic solvent. The solvent may also be water-tolerant. The solvent may have one or more functional groups including, for example, ether, ester, ketone, alcohol, and halo.

In certain embodiments, the solvent system includes an ether, which may include cyclic ethers, polyethers, glycol ethers, and other copolyethers. Suitable ether solvents may include dioxane, dioxin, glyme, diglyme, triglyme, tetrahydrofuran, and any combinations or mixtures thereof. In one embodiment, the solvent system includes 1,4-dioxane. In another embodiment, the solvent system includes triglyme.

In other embodiments, the solvent system includes dimethylacetamide (e.g., N,N-dimethylacetamide), dimethylformamide (e.g., N,N-dimethylformamide), acetonitrile, sulfolane, dioxane, dioxane, dimethyl ether, diethyl ether, glycol dimethyl ether (glyme), diethylene glycol dimethyl ether (diglyme), triethylene glycol dimethyl ether (triglyme), tetraethylene glycol dimethyl ether (tetraglyme), tetrahydrofuran, ethylene glycol, diethylene glycol, triethylene glycol, polyethylene glycol, cyclobutanone, cyclopentanone, cyclohexanone, cycloheptanone, cyclooctanone, methyl acetate, ethyl acetate, propyl acetate, butyl acetate, methyl lactate, ethyl lactate, propyl lactate, butyl lactate, triacetin, dibutylphthalate, butane, pentane, cyclopentane, hexane, cyclohexane, heptane, cycloheptane, octane, cyclooctane, nonane, decane, undecane, dodecane, hexadecane, tetrachloride, chloroform, dichloromethane, nitromethane, toluene, anisole, nitrobenzene, bromobenzene, methylpyrrole (e.g., N-methylpyrrole), methylpyrrolidinone (e.g., N-methylpyrrolidinone), dimethylfuran (e.g., 2,5-dimethylfuran), dichlorobenzene (e.g., o-dichlorobenzene), water, para-xylene, mesitylene, dodecylbenzene, pentylbenzene, hexylbenzene, Wibaryl® A, Wibaryl® B, Wibaryl® AB, Wibaryl® F, Wibaryl® R, Cepsa Petrepar® 550-Q, Santovac®, diphenyl ether, methyldiphenyl ether, ethyldiphenyl ether, water, or any combinations or mixtures thereof. In certain embodiments, the solvent system includes dioxane, dodecane, hexadecane, mesitylene, 2,5-dimethylfuran, para-xylene, or any combinations or mixtures thereof. In one embodiment, the solvent system includes dioxane, dodecane, para-xylene, or any combinations or mixtures thereof.

In certain embodiments, the solvent system includes water, aliphatic solvents (which may be branched or linear), aromatic solvents, or alkyl benzene solvents. In one embodiment, the solvent system includes diphenyl ether or alkyldiphenyl ether.

In yet other embodiments, the solvent system includes an ionic liquid. Suitable ionic liquids may include, for example, 1-allyl-3-methylimidazolium bromide, 1-benzyl-3-methylimidazolium tetrafluoroborate, or any combination or mixture thereof.

It is understood that any description of catalyst for use in the methods described herein may be combined with any descriptions of the solvents the same as if each and every combination were individually listed.

For example, in some embodiments:
(i) the catalyst is a metal chloride, metal triflate, metal acetate or metal acetylacetonate; and
(ii) the solvent system includes an ether, a $C_{8+}$ alkyl solvent (e.g., decane, dodecane), or para-xylene.

In some embodiments:
(i) the catalyst is a metal chloride, metal triflate, metal acetate or metal acetylacetonate; and
(ii) the solvent system includes an ether, a $C_{4+}$ alkyl solvent (e.g., decane, dodecane), para-xylene, or any mixtures or combinations thereof.

In certain embodiments, the catalyst is a metal triflate; and the solvent system includes dioxane or dodecane, or a mixture of combination thereof. In other embodiments, the solvent system further includes para-xylene as a solvent. In yet other embodiments, the catalyst is a metal triflate; and the solvent system includes para-xylene.

In certain embodiments:
(i) the catalyst is a copper chloride, copper triflate, or yttrium triflate; and
(ii) the solvent system includes an ether, a $C_{4+}$ alkyl solvent), para-xylene, or any mixtures or combinations thereof.

In one embodiment, the catalyst is copper (I) triflate. In another embodiment, the catalyst is copper (II) triflate.

In certain embodiments:
(i) the catalyst is copper chloride, copper triflate, or yttrium triflate; and
(ii) the solvent system includes dioxane, dodecane, para-xylene, or any mixtures or combinations thereof.

In one embodiment, the catalyst is copper (I) triflate. In another embodiment, the catalyst is copper (II) triflate. In certain embodiments:
(i) the catalyst is copper triflate; and
(ii) the solvent system includes a mixture of para-xylene and a $C_{8+}$ alkyl solvent.

In one embodiment, the catalyst is copper (I) triflate. In another embodiment, the catalyst is copper (II) triflate. In one embodiment, the $C_{8+}$ alkyl solvent is dodecane.

In certain embodiments:
(i) the catalyst is a sulfonic acid; and
(ii) the solvent system includes an ether, a $C_{8+}$ alkyl solvent, para-xylene, or any mixtures or combinations thereof.

In certain embodiments:
(i) the catalyst is a sulfonic acid; and
(ii) the solvent system includes dioxane, dodecane, para-xylene, or any mixtures or combinations thereof.

In certain embodiments:
(i) the catalyst is triflic acid; and
(ii) the solvent system includes an ether, a $C_{4+}$ alkyl solvent, para-xylene, or any mixtures or combinations thereof.

In certain embodiments:
(i) the catalyst is triflic acid; and
(ii) the solvent system includes dioxane, dodecane, hexadecane, para-xylene, or any mixtures or combinations thereof.

In certain embodiments:
(i) the catalytic is triflic acid; and
(ii) the solvent system includes a $C_{4+}$ alkyl solvent.

In one embodiment:
(i) the catalytic is triflic acid; and
(ii) the solvent system include dodecane or hexadecane.

In certain embodiments:
(i) the catalyst is a metal triflate, triflic acid, or a heteropolyacid; and
(ii) the solvent includes an ether or n-alkane.

In one embodiment, the catalyst is a metal triflate selected from $La(OTf)_3$, $Nd(OTf)_3$, $Sc(OTf)_3$, $Cu[N(Tf)_2]_2$, $Y(OTf)_3$, $[Cu(I)OSO_2CF_3]_2C_6H_6$, and any combination thereof. In another embodiment, the catalyst is triflic acid. In yet another embodiment, the heteropolyacid is $H_4[SiMo_{12}O_{40}] \times H_2O$, $H_3[PMO_{12}O_{40}] \times H_2O$, or any combination thereof. In one embodiment, the solvent system includes an ether, such as dioxane or triglyme. In another embodiment, the solvent system includes an alkane, such as dodecane.

In certain embodiments:
(i) the catalyst is a heteropolyacid; and
(ii) the solvent system includes an ether, a $C_{8+}$ alkyl solvent (e.g., decane, dodecane), para-xylene, or any mixtures or combinations thereof.

In certain embodiments:
(i) the catalyst is a heteropolyacid; and
(ii) the solvent system includes dioxane, dodecane, para-xylene, or any mixtures or combinations thereof.

In certain embodiments:
(i) the catalyst is aluminum chloride; and
(ii) the solvent system includes an ether, a $C_{8+}$ alkyl solvent (e.g., decane, dodecane), para-xylene, or any mixtures or combinations thereof.

In certain embodiments:
(i) the catalyst is aluminum chloride; and
(ii) the solvent system includes dioxane, dodecane, para-xylene, or any mixtures or combinations thereof.

In one embodiment:
(i) the catalyst is copper chloride, copper triflate, yttrium triflate, copper acetate or copper acetylacetonate; and
(ii) the solvent system includes dioxane, triglyme, or any mixtures or combinations thereof.

In one embodiment:
(i) the catalyst is copper triflate or yttrium triflate; and
(ii) the solvent system includes dioxane or triglyme.

In another embodiment:
(i) the catalyst is copper triflate or yttrium triflate; and
(ii) the solvent system includes a $C_{8+}$ alkyl solvent (e.g., decane, dodecane).

In yet another embodiment:
(i) the catalyst is copper triflate or yttrium triflate; and
(ii) the solvent system includes para-xylene.

In yet another embodiment, the catalyst is copper triflate, and the solvent system includes an ether, such as dioxane or triglyme. In yet another embodiment, the catalyst is copper acetate or copper acetylacetonate, and the solvent system includes an ether, such as dioxane or triglyme.

It should further be understood that the catalyst/solvent combinations described above may be used for a reaction using HD as the starting material, DMF as the starting material, or both HD and DMF as the starting materials.

For example, provided is a method for producing para-xylene, by: combining a starting material, ethylene, a solvent system and a catalyst to form a reaction mixture, wherein the starting material is 2,5-dimethylfuran, 2,5-hexanedione, or a combination thereof; and producing para-xylene from at least a portion of the starting materials in the reaction mixture.

Provided is a method for producing para-xylene, by:

a) providing a starting material, wherein the starting material is 2,5-dimethylfuran; b) providing ethylene;

c) providing a catalyst, wherein the catalyst is a metal chloride, a metal triflate, a metal acetate, a metal acetylacetonate, or a heteropolyacid;

d) providing a solvent system, wherein the solvent system includes an ether, a $C_{8+}$ alkyl solvent, an aromatic solvent, an ionic liquid, or any mixtures or combinations thereof;

e) combining the starting material, the ethylene, the solvent system and the catalyst to form a reaction mixture; and f) producing para-xylene from at least a portion of the starting material in the reaction mixture.

In certain embodiments to produce para-xylene from 2,5-dimethylfuran, the catalyst is copper chloride, copper triflate, yttrium triflate, copper acetate or copper acetylacetonate. In certain embodiments to produce para-xylene from 2,5-dimethylfuran, the solvent system includes dioxane, dodecane, decane, para-xylene, diphenyl ether, alkyldiphenyl ether, or any mixtures or combinations thereof.

Provided is also a method for producing para-xylene, by:

a) providing a starting material, wherein the starting material is 2,5-dimethylfuran, 2,5-hexanedione, or a combination thereof;

b) providing ethylene;

c) providing a catalyst, wherein the catalyst is a heteropolyacid or a sulfonic acid;

d) providing a solvent system;

e) combining the starting material, the ethylene, the solvent system and the catalyst to form a reaction mixture; and f) producing para-xylene from at least a portion of the starting materials in the reaction mixture.

In certain embodiments to produce para-xylene from 2,5-dimethylfuran, 2,5-hexanedione, or a combination thereof, the solvent system includes dioxane, dodecane, decane, hexadecane, 2,5-dimethylfuran, para-xylene, diphenyl ether, alkyldiphenyl ether, or any mixtures or combinations thereof.

In yet other embodiments, at least a portion of the DMF (if present), HD (if present), or a combination thereof is converted to para-xylene at a temperature of at least 150° C., or between 150° C. and 300° C.

The para-xylene produced by any of the methods described above may be used for the manufacture of a plastic or a fuel.

Provided is also a method for producing terephthalic acid from para-xylene, by:

a) producing para-xylene according to any of the methods described herein; and b) oxidizing the para-xylene to produce terephthalic acid.

DETAILED DESCRIPTION

The following description sets forth numerous exemplary configurations, methods, parameters, and the like. It should be recognized, however, that such description is not intended as a limitation on the scope of the present disclosure, but is instead provided as a description of exemplary embodiments.

The following description relates to methods of producing compounds of formula I:

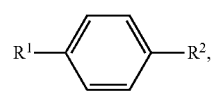

(I)

from a compound of formula A or a compound of formula B:

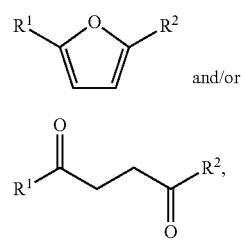

wherein each $R^1$ and $R^2$ is independently hydrogen, alkyl, cycloalkyl, heterocycloalkyl, aryl, or heteroaryl. $R_1$ and $R_2$ may be the same or different substituents. In certain embodiments, each $R^1$ and $R^2$ is independently hydrogen or alkyl.

In some embodiments, the compound of formula I is para-xylene (PX), the compound of formula A is 2,5-dimethylfuran (DMF), and the compound of formula B is 2,5-hexanedione (HD). Thus, provided are methods of producing para-xylene (PX) from 2,5-dimethylfuran (DMF), 2,5-hexanedione (HD), or a combination thereof.

In one aspect, provided is a method of producing a compound of formula I (e.g., para-xylene), by: combining a compound of formula A (e.g., DMF), a compound of formula B (e.g., HD), or a combination thereof, with ethylene, a catalyst, and optionally a solvent to form a reaction mixture; and producing para-xylene from at least a portion of the compound of formula A (e.g., DMF), the compound of formula B (e.g., HD), or a combination thereof, in the reaction mixture.

The use of the particular catalysts, solvents (as the case may be), and reaction conditions provided herein allow for either a compound of formula A (e.g., DMF), a compound of formula B (e.g., HD), or a combination thereof, to serve as a starting material(s) for the production of a compound of formula I (e.g., para-xylene).

Starting Materials

Compounds of Formula A and Compounds of Formula B

One or more compounds of formula A and/or one or more compounds of formula B:

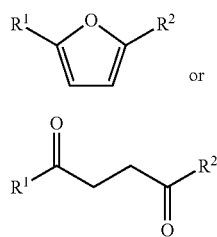

may be used as starting materials for the production of one or more compounds of formula I:

according to the methods described herein.

In certain embodiments, each $R^1$ and $R^2$ is independently hydrogen, alkyl, cycloalkyl, heterocycloalkyl, aryl, or heteroaryl. In certain embodiments, each $R^1$ and $R^2$ is independently hydrogen or alkyl. In certain embodiments, each $R^1$ and $R^2$ is independently a $C_{1-10}$ or a $C_{1-6}$ or a $C_{1-4}$ alkyl. In one embodiment, $R^1$ and $R^2$ are each methyl. In another embodiment, $R^1$ is methyl, and $R^2$ is hydrogen.

In certain embodiments, the methods involve using a compound of formula A. For example, in one embodiment, 2,5-dimethylfuran is used in the methods provided herein to produce para-xylene. In another embodiment, 2-methylfuran is used in the methods provided herein to produce para-xylene. In certain embodiments, the methods involve using a compound of formula B. For example, in one embodiment, 2,5-hexanedione is used in the methods provided herein to produce toluene. In another embodiment, 4-oxopentanal is used in the methods provided herein to produce toluene.

In certain embodiments, the methods involve using a mixture of compounds of formula A to produce a mixture of compounds of formula I. For example, in one embodiment, 2,5-dimethylfuran and 2-methylfuran may be used in the methods provided herein to produce a mixture of para-xylene and toluene. In other embodiments, the methods involve using a mixture of compounds of formula B to produce a mixture of compounds of formula I. For example, in one embodiment, 2,5-hexanedione and 4-oxopentanal may be used in the methods provided herein to produce a mixture of para-xylene and toluene. In yet other embodiments, the methods involve using a mixture of compounds of formula A and compounds of formula B to produce a mixture of compounds of formula I. For example, in one embodiment, 2,5-dimethylfuran, 2-methylfuran, 2,5-hexanedione and 4-oxopentanal may be used in the methods provided herein to produce a mixture of para-xylene and toluene.

"Alkyl" refers to a monoradical unbranched or branched saturated hydrocarbon chain. In some embodiments, alkyl as used herein, such as in compounds of formula I, (A) or (B), has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl.

"Cyclcloalkyl" refers to a cyclic alkyl group. In some embodiments, cycloalkyl as used herein, such as in compounds of formula I, (A) or (B), has from 3 to 20 ring carbon atoms (i.e., $C_{3-20}$ cycloalkyl), or 3 to 12 ring carbon atoms (i.e., $C_{3-12}$ cycloalkyl), or 3 to 8 ring carbon atoms (i.e., $C_{3-8}$ cycloalkyl). Examples of cycloalkyl groups include cyclopropyl, cyclobutyl, cyclopentyl, and cyclohexyl.

"Heterocycloalkyl" refers to a cyclic alkyl group, with one or more ring heteroatoms independently selected from nitrogen, oxygen and sulfur. In some embodiments, the heterocycloalkyl as used herein, such as in compounds of formula I, (A) or (B), has 2 to 20 ring carbon atoms (i.e., $C_{2-20}$ heterocycloalkyl), 2 to 12 ring carbon atoms (i.e., $C_{2-12}$ heterocycloalkyl), or 2 to 8 ring carbon atoms (i.e., $C_{2-8}$ heterocycloalkyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen. In one example, a heterocycloalkyl has 2 to 8 ring carbon atoms, with 1 to 3 ring heteroatoms independently selected from nitrogen, oxygen and sulfur. Examples of heterocycloalkyl groups may include pyrrolidinyl, piperidinyl, piperazinyl, oxetanyl, dioxolanyl, azetidinyl, and morpholinyl.

"Aryl" refers to an aromatic carbocyclic group having a single ring (e.g., phenyl), multiple rings (e.g., biphenyl), or multiple fused rings (e.g., naphthyl, fluorenyl, and anthryl), In certain embodiments, aryl as used herein, such as in compounds of formula I, (A) or (B), has 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more an groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein, such as in compounds of formula I, (A) or (B), has 3 to 20 ring carbon atoms (i.e., $C_{3-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include pyridyl, pyridazinyl, pyrimidinyl, benzothiazolyl, and pyrazolyl. Heteroaryl does not encompass or overlap with aryl as defined above.

The term "substituted", as used herein, means that any one or more hydrogen atoms on the designated atom or group is replaced with a moiety other than hydrogen, provided that the designated atom's normal valence is not exceeded.

Further, it should be understood that when a range of values is listed, it is intended to encompass each value and sub-range within the range. For example, "$C_{1-6}$ alkyl" (which may also be referred to as 1-6C alkyl, C1-C6 alkyl, or C1-6 alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The compounds of formula A and the compounds of formula B used in the methods described herein can be obtained from any source (including any commercially available sources), or be produced by any methods known in the art. Further, it should be understood that the compound of formula B may be generated in situ from the reaction mixture.

For example, DMF used in the methods described herein may be commercially available, or be derived from carbonaceous materials. Examples of suitable carbonaceous materials from which DMF can be derived include agricultural materials (e.g., corn stover, rice hulls, peanut hulls, spent grains, pine chips), processing waste (e.g., paper sludge), recycled cellulosic materials (e.g., cardboard, old corrugated containers (OCC), mixed paper, old newspaper (ONP)), as well as fructose (e.g., high fructose corn syrup), sucrose, glucose, or starch. Various methods are known in the art to obtain DMF from biomass. For example, cellulose and hemicellulose (if present) or other six-carbon sugars (e.g., glucose, fructose) may be converted into 5-chloromethylfurfural, which may be converted into DMF either directly or via 5-hydroxymethylfurfural. See e.g., Chidambaram & Bell, *Green Chem.*, 2010, 12, 1253-1262.

In another example, HD (also known as acetonyl acetone) used in the methods described herein may be commercially available, or be prepared according to methods known in the art. For example, it is known that HD can be prepared by oxidization of allylacetone. See U.S. Pat. No. 3,947,521. HD can also be prepared by hydrolysis of the lactone of alpha-acetyl-gamma-cyano-gamma-hydroxyvaleric acid. See U.S. Pat. No. 3,819,714. Further, it should be understood that HD may be generated in situ from the reaction mixture.

Ethylene

Ethylene is also a starting material for this reaction. The ethylene provided for the methods described herein may be obtained from any source (including any commercially available sources). For example, ethylene can be obtained from fossil fuel sources or renewable sources, such as by dehydration of ethanol (e.g., fermentation-based ethanol).

Catalysts

Various catalysts may be used in the method to convert compounds of formula A (e.g., DMF) and/or compounds of formula B (e.g., HD) into compounds of formula I (e.g., para-xylene). For example, the catalysts may be selected from one or more classes of catalysts, including (i) metal-containing catalysts, including metal-containing salts that are catalytic or may convert in situ into a catalytic species, and (ii) acids (e.g., Lewis acids, weak acids, sulfonic acids, heteropolyacids).

It should be understood, however, that the catalyst may fall into one or more classes listed herein. For example, the catalyst may be copper triflate, which is a metal-containing catalyst and also a Lewis acid. The catalyst may also be supported or unsupported. The catalyst may also be homogeneous or heterogeneous based on the solvent system used in the reaction. The catalysts may also be in the form of a solvate, including, for example, a hydrate. The catalysts may also be a polymer.

It should also be understood that the catalyst increases the rate of the chemical reaction, and such increase may be caused directly or indirectly (e.g., by conversion in situ into a different catalyst species). For example, the catalyst used may be copper triflate. Without wishing to be bound by any theory, under certain reaction conditions, the copper triflate may yield triflic acid, which may contribute to the increase in rate of the chemical reaction. In another example, the catalyst used may be triflimide. In another example, Without wishing to be bound by any theory, the triflimide may yield triflic acid in the reaction mixture, which may contribute to the increase in rate of the chemical reaction.

The catalysts provided for the methods described herein to produce compounds of formula I (e.g., para-xylene) may be obtained from any sources (including any commercially available sources), or may be prepared by any methods or techniques known in the art. It should also be understood that providing a catalyst includes providing the catalyst itself, or a precursor that forms a catalytic species (e.g., in situ) that may contribute to the increase in rate of the chemical reaction.

Metal Catalysts

In some embodiments, the catalyst is a metal catalyst. A metal catalyst can be any catalyst that is a metal or contains a metal ligand. The metals may include, for example, alkali metals, alkali earth metals, transition metals or lanthanides. In one embodiment, the metals may include transition metals or lanthanides. In certain embodiments, the metal is selected from Group 3, Group 9, Group 10, Group 11, and the lanthanide series. In certain embodiments, the metal is selected from Group 3, Group 9, Group 11, and the lanthanide series.

In some embodiments, the metal is aluminum, bismuth, copper, chromium, iron, gadolinium, indium, nickel, neodymium, lithium, sodium, potassium, rubidium, cesium, beryllium, magnesium, calcium, strontium, barium, lanthanum, scandium, titanium, vanadium, yttrium, zinc, platinum, palladium, silver, gold, thallium, rhenium, mercury, tin, boron, gallium, lead, cobalt, germanium, and cerium.

Without wishing to be bound by any theory, under certain conditions, the catalytic species in the reactions described herein may also be formed in situ by providing suitable precursors. For example, copper metal and chlorine gas may be provided to the reaction to produce copper chloride in situ. It should also be understood that the catalytic species may be formed in situ by reaction between the metal precursor and the ethylene provided in the reaction. For example, under certain conditions, copper triflate is provided to the reaction, and may form a catalytic species with ethylene.

In one embodiment, the metal catalyst is a metal-containing catalyst. Metal-containing catalysts have one or more metal cations and one or more counterions or ligands. For example, the catalyst may be a metal-centered catalyst. In certain embodiments, the metal cation in a metal-containing catalyst may be a transition metal cation or a lanthanide cation. In certain embodiments, the metal cation in a metal-containing catalyst is selected from Group 3, Group 9, Group 10, Group 11, and the lanthanide series. In certain embodiments, the metal cation is selected from Group 3, Group 9, Group 11 and or the lanthanide series. In one embodiment, the metal cation is a Group 11 cation. It should be understood that the group number used for the metals follow the IUPAC or long-form nomenclature, which is well-known in the art.

In some embodiments, the catalyst may have a monovalent metal cation. For example, in certain embodiments, the monovalent metal cation is $Cu^+$, $Li^+$, $Na^+$, $K^+$, $Rb^+$, $Cs^+$, $Ag^+$, $Tl^+$, or $Hg_2^{2+}$. In one embodiment, the monovalent metal cation is $Cu^{1+}$.

In other embodiments, the catalyst may have a divalent metal cation or a trivalent metal cation. For example, in some embodiments, the divalent metal cation is $Cu^{2+}$, $Ni^{2+}$, $Be^{2+}$, $Mg^{2+}$, $Ca^{2+}$, $Sr^{2+}$, $Ba^{2+}$, $Zn^{2+}$, $Pt^{2+}$, $Pd^{2+}$, $Hg^{2+}$, $Sn^{2+}$, $Pb^{2+}$, $Co^{2+}$, or $Ge^{2+}$. In certain embodiments, the divalent metal cation is $Cu^{2+}$, $Co^{2+}$, $Cr^{3+}$, $Ni^{2+}$, $Mg^{2+}$, or $Zn^{2+}$. In certain embodiments, the divalent metal cation is $Cu^{2+}$, $Co^{2+}$, $Ni^{2+}$, or $Zn^{2+}$. In one embodiment, the divalent metal cation is $Cu^{2+}$, $Co^{2+}$, or $Zn^{2+}$. In one embodiment, the divalent metal cation is $Cu^{2+}$.

In some embodiments, the trivalent metal cation is $Al^{3+}$, $Bi^{3+}$, $Cr^{3+}$, $Fe^{3+}$, $Gd^{3+}$, $In^{3+}$, $Nd^{3+}$, $La^{3+}$, $Sc^{3+}$, $Y^{3+}$, $Au^{3+}$, $Tl^{3+}$, $Re^{3+}$, $Sn^{3+}$, $B^{3+}$, $Ga^{3+}$, $Co^{3+}$, or $Ce^{3+}$. In certain embodiments, the trivalent metal cation is $Al^{3+}$, $Bi^{3+}$, $Fe^{3+}$, $Gd^{3+}$, $In^{3+}$, $Nd^{3+}$, $La^{3+}$, $Sc^{3+}$, or $Y^{3+}$. In certain embodiments, the trivalent metal cation is $Al^{3+}$, $Fe^{3+}$, $Gd^{3+}$, $In^{3+}$, $La^{3+}$, or $Y^{3+}$. In one embodiment, the trivalent metal cation is $Al^{3+}$, $Gd^{3+}$, $In^{3+}$, $La^{3+}$, or $Y^{3+}$. In another embodiment, the trivalent metal cation is $Gd^{3+}$, $In^{3+}$, $La^{3+}$, or $Y^{3+}$.

In yet other embodiments, the catalyst may have a tetravalent metal ion.

The metal cations may coordinate with one or more cations. For example, the divalent or trivalent metal cation of the catalyst may coordinate with two or three counterions, respectively. Each counterion may independently be selected from, for example, halides (e.g., chloride, bromide), triflates (—OTf), and carboxylates (e.g. formate, acetate, acetylacetonate). It should be understood, however, that any suitable counterion may be used. In one embodiment, the counterions may be chloride or triflate. It should be understood that the counterions may all be the same, the counterions may all be different, or two counterions may be the same and the third counterion may be different.

In some embodiments, the counterions may be ligands that coordinate with the metal. Ligands may be, cationic, anionic or neutral. For example, the catalyst may be $\eta^2$-ethylene-copper(II)triflate.

In some embodiments, the catalyst is aluminum chloride, aluminum bromide, aluminum triflate, bismuth chloride, bismuth bromide, bismuth triflate, copper chloride, copper bromide, copper triflate, cobalt chloride, cobalt bromide, cobalt triflate, chromium chloride, chromium bromide, chromium triflate, iron chloride, iron bromide, iron triflate, gadolinium chloride, gadolinium bromide, gadolinium triflate, indium chloride, indium bromide, indium triflate, nickel chloride, nickel bromide, nickel triflate, neodymium chloride, neodymium bromide, neodymium triflate, magnesium chloride, magnesium bromide, magnesium triflate, lanthanum chloride, lanthanum bromide, lanthanum triflate, scandium chloride, scandium bromide, scandium triflate, tin chloride, tin bromide, tin triflate, titanium chloride, titanium bromide, titanium triflate, vanadium chloride, vanadium bromide, vanadium triflate, yttrium chloride, yttrium bromide, yttrium triflate, zinc chloride, zinc bromide, zinc triflate, or any combinations thereof.

In certain embodiments, the catalyst is copper chloride, copper triflate, yttrium triflate, scandium triflate, lanthanum triflate, neodymium triflate, copper triflimide, or any combinations thereof. In other embodiments, the catalyst is aluminum chloride, copper chloride, copper triflate, yttrium triflate, or any combination thereof. In one embodiment, the catalyst is copper chloride or copper triflate, or a combination thereof. In another embodiment, the catalyst is copper (II) bis(trifluoromethylsulfonyl)imide (i.e., copper triflimide, also referred to as $Cu[N(Tf)_2]_2$).

In other embodiments, the catalyst is a metal-containing salt catalyst, including any such salts that may convert in situ into a species that is catalyst for the reactions described herein. For example, a metal salt catalyst may include a Group 11 metal with one or more counterion(s). The metal of the metal salt catalyst may be a copper cation. In one embodiment, the catalyst is copper acetate or copper acetylacetonate. As discussed above, any suitable counterions may be present in the metal-containing salt catalyst.

In certain embodiments, the catalyst comprises copper or a copper ion. In one embodiment, the catalyst comprises a copper (I) ion. In another embodiment, the catalyst comprises a copper (II) ion. In one embodiment, the catalyst is $Cu[N(Tf)_2]_2$, $CuCl_2$, $Cu(OCOCH_3)_2$, $Cu(CH_3COCH_2COCH_3)_2$, $Cu(II)(BF_4)_2$, $Cu(i)(BF_4)(CH_3CN)_4$, $[Cu(I)OSO_2CF_3]_2C_6H_6$, $(Cu(I)OSO_2CF_3)(CH_3CN)_4$, or any combination thereof. Such catalysts may be obtained from any commercially available source, or prepared by any suitable methods known in the art. Certain catalysts may also be formed in situ. For example, in one embodiment, copper metal may be provided as a precursor to generate $CuCl_2$ in situ. In another embodiment, copper oxide ($Cu_2O$) may be provided in combination with $HBF_4$ and $CH_3CN$ to generate $Cu(I)(BF_4)(CH_3CN)_4$ in situ. In yet another embodiment, copper oxide ($Cu_2O$) may be provided in combination with $CF_3SO_3H$ and $CH_3CN$ to generate $(Cu(I)OSO_2CF_3)(CH_3CN)_4$ in situ.

Lewis Acids

In some embodiments, the catalyst is a Lewis acid. As used herein, a "Lewis acid" refers to an acid substance that can employ an electron lone pair from another molecule in completing the stable group of one of its own atoms.

It should be understood that one or more of catalysts (including the one or more the metal-containing catalysts) described above may be Lewis acids. For example, the catalyst may be a Lewis acid, such as aluminum chloride, zinc chloride, indium chloride, divalent transition metal ions of copper, nickel or cobalt or mixtures thereof such as $CuCl_2$ or $CoCl_2$, triflates such as the triflate of indium, copper, gadolinium or yttrium, trivalent metal ions from the lanthanide series of elements or mixtures thereof.

The catalyst may be a solvate, including hydrate, or anhydrous. For example, in one embodiment, the catalyst is $CuCl_2 \times 2H_2O$. In another embodiment, the catalyst is $CuCl_2$, wherein less than 5%, less than 4%, less than 3%, less than 2%, or less than 1% of the catalyst is water.

In other embodiments, the catalysts may also include acetic acid, haloacetic acid (e.g., chloroacetic acid, dichloroacetic acid, trichloroacetic acid, fluoroacetic acid, and difluoroacetic acid, trifluoroacetic acid). These acids may be Lewis acids in the reaction. The acids may also be obtained from an anhydride that hydrolyzes into its corresponding acid form in the presence of water. For example, acetic anhydride may contain a small percentage of acetic acid, which acts as a catalyst for the reaction. Additionally, the acetic anhydride in the reaction mixture may further convert into acetic acid in the reaction.

Heteropolyacids

In other embodiments, the Lewis acid is a heteropolyacid. Heteropolyacids is a class of acids that includes a combination of hydrogen and oxygen atoms with certain metals and/or non-metals. The heteropolyacid typically includes at least one addenda atom, oxygen, a hetero atom, and acidic hydrogen atoms. In certain embodiments, the addenda atoms may be selected from one or more metals, including for example, tungsten, molybdenum, or vanadium. In certain embodiments, the hetero atom may be selected from p-block elements, such as silicon or phosphorous. It is understood that any description of the addenda atoms for the heteropolyacids for use in the methods described herein may be combined with any descriptions of the hetero atoms the same as if each and every combination were specifically and individually listed. Suitable heteropolyacids may include, for example, tungstosilicic acid, tungostophosphoric acid, molybdosilicic acid, molybdophosphoric acid. A mixture of heteropolyacids may also be used.

The heteropolyacids may have certain structures that are known in the art. In one embodiment, the heteropolyacid is a Keggin structure, having the formula $H_nXM_{12}O_{40}$, where X is the hetero atom, M is the addenda atom, and n is an integer greater than 0. In another embodiment, the heteropolyacid is a Dawson structure having the formula $H_nX_2M_{18}O_{62}$, where X is the hetero atom, M is the addenda atom, and n in an integer greater than 0.

In one embodiment, the catalyst is a heteropolyacid selected from 12-tungstophosphoric acid, 12-molybdophosphoric acid, 12-tungstosilicic acid, 12-molybdosilicic acid, and any combinations thereof.

In certain embodiments, the catalyst may be a solvate of a heteropolyacid. Suitable solvates may include hydrates or alcohol solvates.

In other embodiments that may be combined with any of the foregoing embodiments, the catalyst that is a heteropolyacid may be unsupported or supported. In one embodiment, the catalyst is a supported heteropolyacid. Suitable solid supports for the heteropolyacids may include, for example, carbon, alumina, silica, ceria, titania, zirconia, niobia, zeolite, magnesia, clays, iron oxide, silicon carbide, aluminosilicates, and any modifications, mixtures or combinations thereof.

Sulfonic Acids, Sulfonamides, and Sulfonimides

In some embodiments, the catalyst is a sulfonic acid, or a salt, ester, anhydride or resin thereof. Sulfonic acids used herein may have a structure of formula of $R^xSO_3H$. In certain embodiments, $R^x$ is alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 8, or 1 to 5, or 1 to 3 substituents independently selected from alkyl, haloalkyl, cycloalkyl, heterocycloalkyl, aryl, heteroaryl, nitro, —OR', —C(O)OR', —C(O)NR'R"—CHO, —COR', and cyano, and wherein each R' and R" is independently hydrogen, alkyl, or haloalkyl. In certain embodiments, $R^x$ is alkyl or haloalkyl. In another embodiment, R' is alkyl. In certain embodiments, $R^x$ is a C1-C10 alkyl, or a C1-C10 haloalkyl. In certain embodiments, $R^x$ is methyl, ethyl, propyl, $CHF_2$, $CH_2F$, or $CF_3$. In certain embodiments, the alkyl or haloalkyl may be further substituted with an ether moiety. For example, the alkyl or haloalkyl may be further substituted with —OR', where R' is alkyl or haloalkyl. In other embodiments, $R^x$ is alkyl, haloalkyl, or aryl optionally substituted with alkyl, haloalkyl, or nitro.

As used herein, "haloalkyl" refers to an unbranched or branched chain alkyl group, wherein one or more hydrogen atoms are replaced by a halogen. For example, where a residue is substituted with more than one halogen, it may be referred to by using a prefix corresponding to the number of halogen moieties attached. For example, dihaloalkyl or trihaloalkyl refers to alkyl substituted with two ("di") or three ("tri") halo groups, which may be, but are not necessarily, the same halogen; thus, for example, 2-chloro-2-fluorobutyl is within the scope of dihaloalkyl. An alkyl group in which each H is replaced with a halo group is referred to as a "perhaloalkyl." One example of a perhaloalkyl group is trifluoromethyl (—$CF_3$).

The sulfonic acids used in the methods described herein may include, for example, $CF_3SO_3H$ (i.e., triflic acid), $HCF_2CF_2SO_3H$, $C_6F_5SO_3H$, 4-methylbenzenesulfonic acid (i.e., p-toluene-sulfonic acid), or 2,4-dinitrobenzenesulfonic acid. In one embodiment, the sulfonic acid is triflic acid. In yet another embodiment, the sulfonic acid is p-toluenesulfonic acid.

Salts of sulfonic acids used herein may have the structure of formula $Q^{r+}[R^x SO_3^-]_r$ wherein: Q is a cation; $R^x$ is as described above for sulfonic acids; and r is the charge of the cation. In some embodiments, $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

The salts of the sulfonic acids used in the methods described herein may include, for example, is $Al(OTf)_3$, $Bi(OTf)_3$, $Cu(OTf)_2$, $Cu(OTf)$, $Cr(OTf)_3$, $Fe(OTf)_3$, $Gd(OTf)_3$, $In(OTf)_3$, $Ni(OTf)_2$, $Nd(OTf)_3$, $Rb(OTf)$, $Cs(OTf)$, $Mg(OTf)_2$, $La(OTf)_3$, $Sc(OTf)_3$, $Ti(OTf)_4$, $V(OTf)_5$, $Y(OTf)_3$, $Zn(OTf)_2$, $Pt(OTf)_2$, $Pd(OTf)_2$, $AgOTf$, $Au(OTf)_3$, $Tl(OTO)_3$, $Tl(OTf)$, $Re(OTf)_3$, $Hg_2(OTf)_2$, $Hg(OTf)_2$, $NH_4(OTf)$, $Sn(OTf)_4$, $Sn(OTf)_3$, $Sn(OTf)_2$, $B(OTf)_3$, $Ga(OTf)_3$, $Pb(OTf)_4$, $Pb(OTf)_2$, $Co(OTf)_3$, $Co(OTf)_2$, $Ge(OTf)_4$, $Ge(OTf)_3$, $Ge(OTf)_2$, $Ge(OTf)$, $Ce(OTf)_4$, $Ce(OTf)_3$, or any combinations thereof.

In certain embodiments, the sulfonic acid salt may be in the form of an ionic liquid. In yet other embodiments, the sulfonic acid may be a hydrate. In other embodiments, the sulfonic acid may be anhydrous. For example, the catalyst may be triflic anhydride. In other embodiments, the catalyst is a quaternary amine triflate.

In yet other embodiments, the sulfonic acid catalyst may be a sulfonic acid polymer, including for example, a sulfonic acid resin. In some embodiments, the sulfonic acid resin is a halosulfonic acid resin. In certain embodiments, the sulfonic acid resin is a fluorosulfonic acid resin. In one embodiment, the sulfonic acid resin is $R^{x1}CF_2SO_3H$, where $R^{x1}$ is alkyl or haloalkyl. For example, the sulfonic acid resin is a sulfonated tetrafluoroethylene polymer, such as Nafion.

The catalyst may, in some embodiments, be a sulfonate having the formula $R^xSO_3Si(R^m)_3$, wherein $R^x$ is as defined above for sulfonic acids; and $R^m$ at each occurrence is independent alky or haloalykl. For example, the salt of the sulfonic acid is trimethylsilyltrifluoromethanesulfonate.

In some embodiments, the catalyst is a sulfonamide, or a salt thereof. Sulfonamides used herein may have a structure of formula of $(R^{y1}SO_2)NH_2$ or $(R^{y1}SO_2)NH(R^z)$. In certain embodiments, $R^{y1}$ and $R^z$ are each independently alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 8, or 1 to 5, or 1 to 3 substituents independently selected from alkyl, haloalkyl, cycloalkyl, heterocycloalkyl, aryl, heteroaryl, nitro, —OR', —C(O)OR', —C(O)NR'R"—CHO, —COR', and cyano, and wherein each R' and R" is independently hydrogen, alkyl, or haloalkyl. In certain embodiments, $R^{y1}$ and $R^z$ are each independently alkyl or haloalkyl. In another embodiment, $R^{y1}$ and $R^z$ are each independently alkyl. In certain embodiments, $R^{y1}$ and IV are each independently a C1-C10 alkyl, or a C1-C10 haloalkyl. In certain embodiments, $R^{y1}$ and $R^z$ are each independently methyl, ethyl, propyl, $CHF_2$, $CH_2F$, or $CF_3$. In certain embodiments, the alkyl or haloalkyl may be further substituted with an ether moiety. For example, the alkyl or haloalkyl may be further substituted with —OR', where R' is alkyl or haloalkyl. In other embodiments, $R^{y1}$ and $R^z$ are each independently alkyl, haloalkyl, or aryl optionally substituted with alkyl, haloalkyl, or nitro.

Salts of the sulfonamides used herein may have the structure of formula $Q^{r+}[R^{y1}SO_2)N(R^z)]_r$, or $Q^{r+}[R^{y1}SO_2)NH]_r$, wherein: Q is a cation; $R^{y1}$ and $R^z$ (if present) is as described above for sulfonamides; and r is the charge of the cation. In some embodiments, $Q^{r+}$ is $Al^{3+}$, $B^{3+}$, $Cu^{2+}$, $Cu^+$, $Cr^{3+}$, $Fe^{3+}$, $Gd^{3+}$, $In^{3+}$, $N^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

In some embodiments, the catalyst is a sulfonimide, or a salt thereof. Sulfonimides used herein may have a structure of formula $(R^{y1}SO_2)NH(SO_2R^{y2})$. In certain embodiments, $R^{y1}$ and $R^{y2}$ are each independently alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 8, or 1 to 5, or 1 to 3 substituents independently selected from alkyl, haloalkyl, cycloalkyl, heterocycloalkyl, aryl, heteroaryl, nitro, —OR', —C(O)OR', —C(O)NR'R"—CHO, —COR', and cyano, and wherein each R' and R" is independently hydrogen, alkyl, or haloalkyl. In certain embodiments, $R^{y1}$ and $R^{y2}$ are each independently alkyl or haloalkyl. In another embodiment, $R^{y1}$ and $R^{y2}$ are each independently alkyl. In certain embodiments, $R^{y1}$ and $R^{y2}$ are each independently a C1-C10 alkyl, or a C1-C10 haloalkyl. In certain embodiments, $R^{y1}$ and $R^{y2}$ are each independently methyl, ethyl, propyl, $CHF_2$, $CH_2F$, or $CF_3$. In certain embodiments, the alkyl or haloalkyl may be further substituted with an ether moiety. For example, the alkyl or haloalkyl may be further substituted with —OR', where R' is alkyl or haloalkyl. In other embodiments, $R^x$ is alkyl, haloalkyl, or aryl optionally substituted with alkyl, haloalkyl, or nitro.

The sulfonimides used in the methods described herein may include, for example, $NH(Tf)_2$ (i.e., triflimide). It should be understood that, as used herein, "-Tf" refers to triflyl.

Salts of sulfonimides used herein may have the structure of formula $Q^{r+}[(R^{y1}SO_2)N(R^{y2}SO_2)]_r$, wherein: Q is a cation; $R^{y1}$ and $R^{y2}$ are as described above for sulfonimides; and r is the charge of the cation. In some embodiments, $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

The salts of sulfonimides used herein may include, for example, $Al[N(Tf)_2]_3$, $Bi[N(Tf)_2]_3$, $Cu[N(Tf)_2]_2$, $Cu[N(Tf)_2]$, $Cr[N(Tf)_2]_3$, $Fe[N(Tf)_2]_3$, $Gd[N(Tf)_2]_3$, $In[N(Tf)_2]_3$, $Ni[N(Tf)_2]_2$, $Nd[N(Tf)_2]_3$, $Li[N(Tf)_2]$, $Na[N(Tf)_2]$, $K[N(Tf)_2]$, $Rb[N(Tf)_2]$, $Cs[N(Tf)_2]$, $Mg[N(Tf)_2]_2$, $Ba[N(Tf)_2]_2$, $Ca[N(Tf)_2]_2$, $La[N(Tf)_2]_3$, $Sc[N(Tf)_2]_3$, $Ti[N(Tf)_2]_4$, $V[N(Tf)_2]_5$, $Y[N(Tf)_2]_3$, $Zn[N(Tf)_2]_2$, $Pt[N(Tf)_2]_2$, $Pd[N(Tf)_2]_2$, $Ag[N(Tf)_2]$, $Ag[N(Tf)_2]_2$, $Au[N(Tf)_2]_3$, $Tl[N(Tf)_2]_3$, $Tl[N(Tf)_2]$, $Re[N(Tf)_2]_3$, $Hg_2[N(Tf)_2]_2$, $Hg[N(Tf)_2]_2$, $NH_4[N(Tf)_2]$, $Sn[N(Tf)_2]_4$, $Sn[N(Tf)_2]_3$, $Sn[N(Tf)_2]_2$, $B[N(Tf)_2]_3$, $Ga[N(Tf)_2]_3$, $Pb[N(Tf)_2]_4$, $Pb[N(Tf)_2]_2$, $Co[N(Tf)_2]_3$, $Co[N(Tf)_2]_2$, $Ge[N(Tf)_2]_4$, $Ge[N(Tf)_2]_3$, $Ge[N(Tf)_2]_2$, $Ge[N(Tf)_2]$, $Ce[N(Tf)_2]_4$, $Ce[N(Tf)_2]_3$, or any combinations thereof. In other embodiments, the salt of the sulfonimide is ethyldimethylpropylammonium bis(trifluoromethylsulfonyl)imide, 1-butyl-1-methylpyrrolidinium bis(trifluoromethylsulfonyl)imide, 1-ethyl-3-methylimidazolium bis(trifluoromethylsulfonyl)imide, 1-butyl-3-methylimidazolium bis(trifluoromethylsulfonyl)imide, 1-allyl-3-methylimidazolium bis(trifluoromethylsulfonyl)imide, triethylsulfonium bis(trifluoromethylsulfonyl)imide, trihexyltetradecylphosphonium bis(trifluoromethylsulfonyl)amide, 1,2-dimethyl-3-propylimidazolium bis(trifluoromethylsulfonyl)imide, $[(C_6H_{13})_3(C_{14}H_{29})P]^+[(CF_3SO_2)_2)_2N]^-$, $[C_{11}H_{16}N]^+[N(SO_2CF_3)_2]$, $[C_8H_{15}N_2]^+[N(SO_2CF_3)_2]$, $[C_6H_{11}N_2]^+[N(SO_2CF_2CF_3)_2]$, $[C_6H_{11}N_2]^+[N(SO_2CF_3)_2]$, $[C_6H_{14}N]^+[N(SO_2CF_3)_2]$, 1-butyl-1-methylpyrrolidinium trifluoromethanesulfonate, 1-ethyl-3-methylimidazolium trifluoromethanesulfonate, 1-butyl-3-methylimidazolium trifluoromethanesulfonate, 1-butyl-3-methylimidazolium trifluoromethanesulfonate, or any combinations thereof. In one embodiment, the salt of the sulfonimide is bis(pentafluoroethylsulfonyl)imide salt.

In yet other embodiments, the salt of the sulfonic acid, sulfonamide, or sulfonimide has a cation, wherein the reduction of the cation to its elemental state (i.e., zero oxidation state) has a standard reduction potential greater than −0.2 eV relative to standard hydrogen potential. Any suitable methods or techniques known in the art may be used to measure standard reduction potential.

Other Acids

Other suitable acids may also be used as the catalyst in the methods described herein. In some embodiments, the acid has a pKa that is lower than the pKa of sulfuric acid. In other embodiments, the acid is $HClO_4$ or $H_2SO_4$.

Water-Tolerant Catalysts

In some embodiments, the catalysts may also be water-tolerant catalysts. As used herein, "a water-tolerant catalyst" refers to a catalyst that is not deactivated by the presence of water in a given reaction. One of skill in the art would recognize that a given catalyst may show water stability for the purposes of one reaction, but not toward another. Water-tolerant catalyst can improve recyclability of the catalyst used in the reaction on industrial scale, since water can often be produced as a by-product in the reaction. In some embodiments, the water-tolerant catalyst may have a $pK_h$ between 4.3 and 10.08. $K_h$ is the hydrolysis constant. $pK_h$ is defined as follows:

$$pK_h = -\log K_{xy}, \text{ where}$$

$$K_{xy} = \frac{[M_x(OH)_y^{(xz-y)+}][H^+]^y}{[M^{z+}]^x} + \frac{g_{xy}g_{H^+}^y}{g_{M^{z+}}^x a_{H_2O}^y},$$

based on the following reaction:

$xM^{z+} + y H_2O \leftrightharpoons M_x(OH)_y^{(xz-y)+} + y H^+$, where M is the metal cation. In other embodiments, the water-tolerant catalyst may have a water exchange rate constant of at least $3.2 \times 10^6$ $M^{-1}s^{-1}$. See generally Kobayashi et al., *J. Am. Chem. Soc.* 1998, 120, 8287-8288.

Examples of water-tolerant catalysts may include those with a metal cation selected from Sc(III), Y(III), Ln(III), Fe(II), Cu(II), Zn(II), Cd(II), Pb(II), La(III), Ce(III), Pr(III), Nd(III), Sm(III), Gd(III), Tb(III), Dy(III), Ho(III), Er(III), Tm(III), Yb(III), and Lu(III). In certain embodiments, the catalyst may include Fe(II), Cu(II), Zn(II), Cd(II), Pb(II)

Sc(III), Ln(III), Mn(II), or Ag(I). Water-tolerant catalysts may include, for example, $ScCl_3$, $Sc(ClO_4)_3$, $Mn(ClO_4)_2$, $FeCl_2$, $Fe(ClO_4)_2$, $FeCl_3$, $Fe(ClO_4)_3$, $Co(ClO_4)_2$, $Ni(ClO_4)_2$, $CuCl_2$, $Cu(ClO_4)_2$, $ZnCl_2$, $Zn(ClO_4)_2$, $YCl_3$, $Y(ClO_4)_3$, $AgClO_4$, $CdCl_2$, $Cd(ClO_4)_2$, $InCl_3$, $In(ClO_4)_3$, $SnCl_2$, $La(OTf)_3$, $Ce(OTf)_3$, $Pr(OTf)_3$, $Nd(OTf)_3$, $Sm(OTf)_3$, $Eu(OTf)_3$, $Gd(OTf)_3$, $Tb(OTf)_3$, $Dy(OTf)_3$, $Ho(OTf)_3$, $Er(OTf)_3$, $Tm(OTf)_3$, $YbCl_3$, $Yb(ClO_4)_3$, $Yb(OTf)_3$, $Lu(OTf)_3$, $PbCl_2$, and $Pb(ClO_4)_2$.

Supported or Unsupported Catalysts

Any of the catalysts described above may be unsupported or supported. In one embodiment, the catalyst is unsupported. In another embodiment, the catalyst is supported by a solid support. Suitable supports may include, for example, carbon, alumina, silica, ceria, titania, zirconia, niobia, zeolite, magnesia, clays, iron oxide, silicon carbide, aluminosilicates, and any modifications, mixtures or combinations thereof. In certain embodiments, the support is silica, alumina, mordenite, carbon (including, for example, activated carbon), or zeolites (e.g., HY zeolite). Examples of supported catalyst may include copper on mordenite, alumina or zeolite. In one embodiment, the catalyst is copper (II) on mordenite, copper chloride on silica, copper chloride on alumina, or copper chloride on HY zeolite. In another embodiment, the support is activated carbon. The activated carbon may also be further treated, for example, acid treated (e.g., $H_3PO_4$ treated).

Solid supported catalysts can more easily be recovered, recycled, and used in a continuous process. When a catalyst support is used, the metals may be deposited using any procedures known in the art. See e.g., Schwarz et al., *Chem. Rev.* 95, 477-510, (1995).

Homogeneous or Heterogeneous Catalysts

In some embodiments, the catalyst is homogeneous in the reaction mixture. As used herein, a "homogeneous catalyst" refers to a catalyst that substantially dissolves in the reaction mixture under the reaction conditions. For example, acetic acid as the catalyst substantially dissolves in dioxane. In another example, copper triflate substantially dissolves in dodecane under the reaction conditions, but not at all conditions (e.g., at standard, temperature and pressure). A catalyst is "substantially dissolved" when the amount of dissolved catalyst exceeds the quantity of undissolved catalyst at the reaction conditions. In some embodiments, the catalyst is substantially dissolved when the ratio of amount of undissolved catalyst to the amount of dissolved catalyst is between 0:1 and 1:1 at the reaction conditions. In one embodiment, the ratio of amount of undissolved catalyst to the amount of dissolved catalyst is about 0 at the reaction conditions. Any suitable methods may be used to determine or quantify the solubility of catalyst.

In one embodiment, the homogeneous catalyst is a sulfonic acid, or a salt, ester, anhydride or resin thereof, a sulfonamide, or a salt thereof, or a sulfonimide, or a salt thereof.

In other embodiments, the catalyst is heterogeneous in the reaction. As used herein, a "heterogeneous catalyst" refers to any catalyst that is not a homogeneous catalyst as described above.

It should be understood that the homogeneity or heterogeneity of a catalyst may depend on the solvent or solvent mixtures used, as well as the reaction conditions.

Amount of Catalyst

The amount of catalyst used may vary depending on the catalyst, starting materials, solvent, and reaction conditions. As used herein, "catalyst loading" refers to the amount of catalyst used in relation to the amount of DMF used, expressed as a weight ratio of DMF (as the starting material) to the catalyst used. For example, in some embodiments, the catalyst loading is between 10 to 500, or between 10 to 300, or between 50 to 500, or between 100 to 500, or between 100 to 300, or between 200 to 500. Under certain conditions, it was surprisingly observed that lowering the amount of catalyst used relative to the amount of DMF used increased selectivity of PX produced.

Further, it should be understood that in certain embodiments, one or more of the catalysts described herein may be used.

Solvent Systems

A solvent, or a combination or mixture of solvents, may also be optionally added to the reaction mixture. The solvent(s) used in the methods described herein dissolve(s) at least a portion of ethylene, compounds of formula A and/or compounds of formula B (if present). The solvents used in the methods described herein may be obtained from any source, including any commercially available sources. In some embodiments, the methods described herein use certain solvents to convert DMF, HD, or a combination thereof, into para-xylene with yields of at least 50%, at least 75%, at least 80%, at least 85%, at least 90%, at least 95%, or at least 99% on a molar basis.

The particular solvents used in the methods described herein typically can solubilize, or at least partially solubilize, the starting materials (e.g., DMF, HD or a combination thereof, ethylene) and/or catalysts, which can help to enhance the solvation effect and improve the reaction rate. For example, in some embodiments, the solvent system has an ethylene solubility between about 0 mol/L and about 0.82 mol/L, between about 0.82 mol/L and about 1.2 mol/L, or between about 1.2 mol/L and about 4.0 mol/L, when ethylene solubility is measured a temperature of about 23° C.

The solvents used may also be selected based on their boiling points. The solvents may be selected based on their boiling points at standard pressure or operating pressure. In some embodiments, the solvent may have a boiling point of between 80° C. and 400° C., or between 150° C. and 350° C., or between 350° C. and 450° C. Further, the solvent, or the combination or mixture of solvents, selected may have a boiling point higher than para-xylene. This would allow para-xylene to be distilled from the reaction mixture, leaving the catalyst and solvent behind to be recycled and/or recovered.

Additionally, the solvents are typically stable to the process conditions, and preferably can be recycled for use again in the reaction. The recyclability of the solvent is particularly useful for performing the methods described herein on a commercial scale.

The solvents used herein may be aliphatic or aromatic. The solvents may also have one or more functional groups such as halo, ester, ether, ketone, and alcohol, or any combinations or mixtures thereof. The solvent may also be non-cyclic (including linear or branched) or cyclic. While the different classes of solvents are described below (e.g., aprotic solvents, aliphatic solvents, aromatic solvents, alkyl phenyl solvents, ether solvents, alcohol solvents, ketone solvents, haloginated solvents, or ionic liquids), it should be understood that the solvent may fall within one or more classes described. For example, dioxane is an ether that is aprotic.

In one embodiment, the solvent system includes dimethylacetamide (e.g., N,N-dimethylacetamide), dimethylformamide (e.g., N,N-dimethylformamide), acetonitrile, sulfolane, dioxane, dioxane, dimethyl ether, diethyl ether, glycol dimethyl ether (monoglyme), ethylene glycol diethyl ether (ethyl glyme), diethylene glycol dimethyl ether (diglyme), diethylene glycol diethyl ether (ethyl digylme), triethylene glycol dimethyl ether (triglyme), diethylene glycol dibutyl ether (butyl diglyme), tetraethylene glycol dimethyl ether (tetraglyme), polyglyme, proglyme, higlyme, tetrahydrofuran, ethylene glycol, diethylene glycol, triethylene glycol, polyethylene glycol, cyclobutanone, cyclopentanone, cyclohexanone, cycloheptanone, cyclooctanone, methyl acetate, ethyl acetate, propyl acetate, butyl acetate, methyl lactate, ethyl lactate, propyl lactate, butyl lactate, triacetin, dibutylphthalate, butane, pentane, cyclopentane, hexane, cyclohexane, heptane, cycloheptane, octane, cyclooctane, nonane, decane, undecane, dodecane, hexadecane, tetrachloride, chloroform, dichloromethane, nitromethane, toluene, anisole, nitrobenzene, bromobenzene, methylpyrrole (e.g., N-methylpyrrole), methylpyrrolidinone (e.g., N-methylpyrrolidinone), dimethylfuran (e.g., 2,5-dimethylfuran), dichlorobenzene (e.g., o-dichlorobenzene), para-xylene, mesitylene, dodecylbenzene, pentylbenzene, hexylbenzene, Wibaryl® A, Wibaryl® B, Wibaryl® AB, Wibaryl® F, Wibaryl® R, Cepsa Petrepar® 550-Q, Santovac®, diphenyl ether, methyldiphenyl ether, ethyldiphenyl ether, water, or any combinations or mixtures thereof.

In certain embodiments, the solvent system includes dioxane, tetrahydrofuran, sulfolane, triglyme, or any combinations or mixtures thereof. In one preferred embodiment, the solvent system includes 1,4-dioxane. In other embodiments, the solvent system includes a glyme. For example, in one embodiment, the solvent system includes triglyme. Any of the above indicated solvents which have these same properties as dioxane or triglyme may be used as a solvent in the methods described herein.

Aprotic Solvents

In some embodiments, the solvent system includes an aprotic solvent. For example, the aprotic solvent may have a dipole moment above 0.1. One of skill in the art would understand that the dipole moment is a measure of polarity of a solvent. The dipole moment of a liquid can be measured with a dipole meter. Suitable aprotic solvents may include, for example, dimethylacetamide, dimethylformamide (including, for example, N,N-dimethylformamide), methylpyrrolidinone (e.g., N-methylpyrrolidinone), dioxane, polyethers (including, for example, glyme, diglyme, triglyme, tetraglyme), acetonitrile, sulfolane, ethers (including, for example, tetrahydrofuran, dialkylether (e.g., dimethylether, diethylether), nitromethane, anisole, nitrobenzene, bromobenzene, chlorobenzene, or any combinations or mixtures thereof.

Aliphatic Solvents

In one embodiment, the solvent system includes an aliphatic solvent. The aliphatic solvent may be linear, branched, or cyclic. The aliphatic solvent may also be saturated (e.g., alkane) or unsaturated (e.g., alkene or alkyne). In some embodiments, the solvent system includes a C1-C20 aliphatic solvent, a C1-C10, aliphatic solvent, or a C1-C6 aliphatic solvent. In certain embodiments, the solvent system includes a C4-C30 aliphatic solvent, a C6-C30 aliphatic solvent, a C6-C24 aliphatic solvent, or a C6-C20 aliphatic solvent. In certain embodiments, the solvent system includes C8+ alkyl solvent, or a C8-C50 alkyl solvent, a C8-C40 alkyl solvent, a C8-C30 alkyl solvent, a C8-C20 alkyl solvent, or a C8-C16 alkyl solvent. Suitable aliphatic solvents may include, for example, butane, pentane, cyclopentane, hexane, cyclohexane, heptane, cycloheptane, octane, cyclooctane, nonane, decane, undecane, dodecane, hexadecane, or any combinations or mixtures thereof. In certain embodiments, the aliphatic solvent is linear.

The aliphatic solvent may be obtained from petroleum refining aliphatic fractions, including any isomers of the aliphatic solvents, and any mixtures thereof. For example, alkane solvents may be obtained from petroleum refining alkane fractions, including any isomers of the alkane solvents, and any mixtures thereof. In certain embodiments, the solvent system includes petroleum refining alkane fractions.

Aromatic Solvents

In another embodiment, the solvent system includes an aromatic solvent. In some embodiments, the solvent system includes a C6-C20 aromatic solvent, a C6-C12 aromatic solvent, or a C13-C20 aromatic solvent. The aromatic solvent may be optionally substituted. Suitable aromatic solvents may include, for example, toluene, anisole, nitrobenzene, bromobenzene, chlorobenzene (including, for example, dichlorobenzene), dimethylfuran (including, for example, 2,5-dimethylfuran), and methylpyrrole (including, for example, N-methylpyrrole). In one embodiment, the solvent system includes para-xylene (which may be produced in the reaction or provided to the reaction system).

Alkyl Phenyl Solvents

As used herein, "an alkyl phenyl solvent" refers to a class of solvents that may have one or more alkyl chains and one or more phenyl or phenyl-containing ring systems. The alkyl phenyl solvent may be referred to as an alkylbenzene or a phenylalkane. One skilled in the art would recognize that certain phenylalkanes may also be interchangeably referred to as an alkylbenzene. For example, (1-phenyl)pentane and pentylbenzene refer to the same solvent.

In some embodiments, the solvent system includes an alkylbenzene. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include pentylbenzene, hexylbenzene and dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl rings.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains.

In some embodiments, the solvent system includes phenylalkane. Examples may include (monophenyl)alkanes, (diphenyl)alkanes, and (polyphenyl)alkanes. In certain embodiments, the phenylalkane has one phenyl ring attached to one alkyl chain. The phenyl ring may be attached to any carbon along the alkyl chain. For example, the phenyl alkyl having one alkyl chain may be (1-phenyl)pentane, (2-phenyl)pentane, (1-phenyl)hexane, (2-phenyl)hexane, (3-phenyl)hexane, (1-phenyl)dodecane, and (2-phenyl)dodecane.

In other embodiments, the phenylalkane has two or more phenyl rings attached to one alkyl chain.

In one embodiment, the solvent system includes Wibaryl® A, Wibaryl® B, Wibaryl® AB, Wibaryl® F, Wibaryl® R, Cepsa Petrepar® 550-Q, Santovac®, or any combinations or mixtures thereof.

In certain embodiments, the alkyl chain of a solvent may be 1 to 20 carbon atoms (e.g., $C_{1-20}$ alkyl). In one embodiment, the alkyl chain may be 4 to 15 carbons (e.g., $C_{4-15}$ alkyl), or 10 to 13 carbons (e.g., $C_{10-13}$ alkyl). The alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the solvent includes two or more alkyl chains, certain alkyl chains may be linear, whereas other alkyl chains may be branched. In other embodiments where the solvent includes two or more alkyl chains, all the alkyl chains may be linear or all the alkyl chains may be branched.

For example, the solvent system includes a linear alkylbenzene ("LAB"). Linear alkylbenzenes are a class of solvents having the formula $C_6H_5C_nH_{2n+1}$. For example, in one embodiment, the linear alkylbenzene is dodecylbenzene. Dodecylbenzene is commercially available, and may be "hard type" or "soft type". Hard type dodecylbenzene is a mixture of branched chain isomers. Soft type dodecylbenzene is a mixture of linear chain isomers. In one embodiment, the solvent system includes a hard type dodecylbenzene.

In some embodiments, the solvent system includes any of the alkyl phenyl solvents described above, in which the phenyl ring is substituted with one or more halogen atoms. In certain embodiments, the solvent system includes an alkyl(halobenzene). For example, the alkyl(halobenzene) may include alkyl(chlorobenzene). In one embodiment, the halo substituent for the phenyl ring may be, for example, chloro, bromo, or any combination thereof.

In other embodiments, the solvent system includes naphthalene, naphthenic oil, alkylated naphthalene, diphenyl, polychlorinated biphenyls, polycyclic aromatic hydrocarbons, or halogenated hydrocarbons.

Ether Solvents

In other embodiments, the solvent system includes an ether solvent, which refers to a solvent having at least one ether group. For example, the solvent system includes a C2-C20 ether, or a C2-C10 ether. The ether solvent can be non-cyclic or cyclic. For example, the ether solvent may be alkyl ether (e.g., diethyl ether, glycol dimethyl ether (glyme), diethylene glycol dimethyl ether (diglyme), or triethylene glycol dimethyl ether (triglyme)). In another example, the ether solvent may be cyclic, such as dioxane (e.g., 1,4-dioxane), dioxin, tetrahydrofuran, or a cycloalkyl alkyl ether (e.g., cyclopentyl methyl ether).

The solvent system may include an acetal such as dioxolane (e.g., 1,3-dioxolane).

The solvent system may also include a polyether with two or more oxygen atoms. In some embodiments, the ether solvent has a formula as follows:

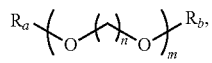

where each $R_a$ and $R_b$ are independently aliphatic moieties, and n and m are integers equal to or greater than 1. In some embodiments, each $R_a$ and $R_b$ are independently alkyl. In certain embodiments, each $R_a$ and $R_b$ are independently C1-C10 alkyl, or C1-C6 alkyl. $R_a$ and $R_b$ may be the same or different. In other embodiments, each n and m are independently 1 to 10, or 1 to 6, where n and m may be the same or different.

The formula above includes proglymes (such as dipropylene glycol dimethylether), or glymes (such as glycol diethers based on ethylene oxide). In one embodiment, the solvent system includes glyme, diglyme, triglyme, or tetraglyme.

It should also be understood that a solvent having an ether group may also have one or more other functional groups. It should be understood, however, that the solvent may have an ether functional group in combination with one or more additional functional groups, such as alcohols. For example, the solvent system includes alkylene glycols (e.g., ethylene glycol, diethylene glycol, triethylene glycol, polyethylene glycol), phenyl ethers (e.g., diphenyl ether, polyphenyl ethers), or alkylphenylethers (e.g., alkyldiphenyl ether).

In certain embodiments, the solvent system includes a polyphenyl ether that includes at least one phenoxy or at least one thiophenoxy moiety as the repeating group in ether linkages. For example, in one embodiment, the solvent system includes Santovac.

Ester Solvents

In yet other embodiments, the solvent system includes an ester solvent, which refers to a solvent having at least one ester group. For example, the solvent system includes a C2-C20 ester, or a C2-C10 ester. The ester solvent can be non-cyclic (linear or branched) or cyclic. For example, non-cyclic ester solvents may include alkyl acetate (e.g., methyl acetate, ethyl acetate, propyl acetate, butyl acetate), triacetin, and dibutylphthalate. An example of cyclic ester is, for example, propylene carbonate. It should be understood, however, that a solvent having an ester group may also have one or more other functional groups. The ester solvent may also include alkyl lactate (e.g., methyl lactate, ethyl lactate, propyl lactate, butyl lactate), which has both an ester group as well as a hydroxyl group.

Alcohol Solvents

In yet other embodiments, the solvent system includes an alcohol, which refers to a solvent having at least hydroxyl group. For example, the solvent can be a C1-C20 alcohol, a C1-C10 alcohol, or a C1-C6 alcohol. Alcohol solvents may include, for example, methanol, ethanol and propanol. The solvent may also be an alkanediol, such as 1,3-propanediol or propylene glycol.

Ketone Solvents

It yet other embodiments, the solvent system includes a ketone. For example, the solvent can be a C2-C20 ketone, a C2-C10 ketone, or a C2-C6 ketone. The ketone solvent can be non-cyclic (linear or branched) or cyclic. For example, the solvent system includes cyclobutanone, cyclopentanone, cyclohexanone, cycloheptanone, or cyclooctanone.

Halogenated Solvents

In yet other embodiments, the solvent system includes halogenated solvents. For example, the solvent can be a chlorinated solvent. Suitable chlorinated solvents may include, for example, carbon tetrachloride, chloroform, methylene chloride, bromobenzene and dichlorobenzene.

Ionic Liquids

The solvent may also be an ionic liquid. Suitable ionic liquids may include, for example, 1-allyl-3-methylimidazolium bromide and 1-benzyl-3-methylimidazolium tetrafluoroborate.

Solvent Combinations or Mixtures

A combination or mixture of solvents may also used in the methods described herein. In some embodiments, an ether solvent may be combined with one or more other types of solvents listed above, including for example an aliphatic solvent. In one embodiment, the solvent combination or mixture is dioxane and an aliphatic solvent. For example, the solvent combination is dioxane and dodecane, or para-xylene and dodecane.

When a combination or mixture of solvents is used, the two or more solvents may be used in any suitable combination to convert DMF and/or HD into PX. For example, when a two-solvent system is used, the two solvents may be present in a weight ratio of about 1 to about 1, or about 1 to about 2, or about 1 to about 3, or about 1 to about 4, or about 1 to about 5. In one embodiment, when the solvent system includes dioxane and dodecane, or para-xylene and dodecane, the two solvents are used in a weight ratio of about 1 to about 1.

Amount of Solvent

The amount of solvent used may vary depending on the starting materials, catalyst used, and reaction conditions. For example, in some embodiments, the concentration of the DMF and/or HD in the reaction mixture is from about 1 to about 75% by weight in the solvent, or from about 3 to about 50% by weight in the solvent. It should also be understood that the amount of solvent used may vary depending on whether the reaction is as a batch or a continuous system. For example in a batch operation, the concentration of the DMF and/or HD in the reaction mixture may start at 50% by weight and end up to be 0.01% by weight.

Ethylene

The ethylene used in the methods described herein may be added using any suitable methods or techniques to the reactor. For example, in certain embodiments, ethylene may be added as a gas into the reactor.

The initial ethylene pressure refers to the pressure at which ethylene (as a gas) is added to the reactor. The ethylene may be added at an initial pressure such that the concentration of this reactant is sufficiently high in the solvent for optimal reaction rates. In some embodiments, the initial ethylene pressure is at least 10 psi, at least 50 psi, at least 75 psi, at least 100 psi, at least 200 psi, at least 250 psi, at least 300 psi, or at least 400 psi. In certain embodiments, the initial ethylene pressure is between 50 psi and 20,000 psi, or between 100 psi and 20,000 psi, or between 300 psi to 20,000 psi, or between 400 psi and 1,000 psi, or between 400 psi and 800 psi, between 600 psi and 1000 psi, between 600 and 6000 psi, or between, between 760 psi and 6000 psi, or between 1000 psi to 6000 psi.

In other embodiments, ethylene may be dissolved, or at least partially dissolved, in one or more solvents described herein and added to the reactor. In certain embodiments, the ethylene solubility in the solvent system is between about 0 mol/L and about 0.82 mol/L, between about 0.82 mol/L and about 1.2 mol/L, or between about 1.2 mol/L and about 4.0 mol/L, when ethylene solubility is measured at temperature of about 23° C.

The ethylene may also be provided at supercritical pressures and/or supercritical temperatures.

Reaction Conditions

The operating temperature refers to the average temperature of the reaction mixture in the vessel. In some embodiments, the operating temperature may be at least 150° C., or at least 200° C. In other embodiments, the operating temperature may be between 100° C. and 300° C., between 150° C. and 400° C., between 150° C. and 300° C., between 125° C. and 175° C., between 200° C. to 350° C., between 200° C. to 250° C., between 200° C. and 400° C., between 270° C. to 400° C., between 220° C. to 230° C., between 250° C. to 300° C., or between 150° C. and 220° C. In one embodiment, the operating temperature is between room temperature (e.g., 18° C.-22° C.) and 300° C. Higher operating temperatures can be used provided that the solvent selected is stable.

The operating pressure refers to the average absolute internal pressure of the vessel. In some embodiments, the reaction may proceed at an operating pressure between 1 bar and 1000 bar, between 10 bar to 1000 bar, between 20 bar to 1000 bar, between 50 bar to 1000 bar, between 100 bar to 1000 bar, between 150 bar to 500 bar, between 35 and 38 bar, between 1 bar and 50 bar, between 1 bar and 40 bar, between 1 bar and 30 bar, between 1 bar and 20 bar, between 1 bar and 10 bar, between 1 bar and 5 bar, between 5 bar and 30 bar, between 5 bar and 20 bar, or between 5 bar and 10 bar. At such operating pressures, the concentration of the ethylene reactant is sufficient high for optimal reaction rates.

In other embodiments, the operating pressure is between 50 psi and 1,000 psi, or between 50 psi and 800 psi, between 50 psi and 700 psi, between 50 psi and 600 psi, or between 600 psi and 1000 psi.

It should be understood that higher operating pressures can be used depending on the equipment available. In other embodiments, the ethylene is near critical where the temperature is between about 270K and about 290K, and the partial operating pressure of ethylene is between about 45 bar and about 65 bar. In other embodiments, the ethylene is supercritical, where the temperature is greater than or equal to about 282K, and the partial operating pressure of ethylene is greater than about 734 psi. In yet other embodiments, the ethylene is supercritical, wherein the temperature is greater than or equal to about 282K and the partial operating pressure of ethylene is greater than or equal to about 734 psi.

It should be understood and clearly conveyed herein that the operating temperature and operating pressure may be the same as if each and every combination were individually listed. For example, in one variation, the method is carried out at an operating temperature of about 225° C. and an operating pressure of about 34 bar (equivalent to about 500 psi).

The methods described herein may also be carried out under supercritical conditions (e.g., supercritical pressures and/or supercritical temperatures). For example, in one embodiment, supercritical conditions may be used if a solvent is not used in the reaction. In one embodiment, the method is carried out at or above 50 bar and/or at or above 9° C. (i.e., 282 K).

It should be understood that temperature may be expressed as degrees Celsius (° C.) or Kelvin (K). One of ordinary skill in the art would be able to convert the temperature described herein from one unit to another. Pressure may also be expressed as gauge pressure (barg), which refers to the pressure in bars above ambient or atmospheric pressure. Pressure may also be expressed as bar, atmosphere (atm), pascal (Pa) or pound-force per square inch (psi). One of ordinary skill in the art would be able to convert the pressure described herein from one unit to another.

The method may be performed with or without stirring. In certain preferred embodiments, the method is performed with stirring to increase conversion and/or selectivity.

Additionally, the method may be carried out batch-wise or continuously. The reaction time (in a batch-wise process) or residence time (in a continuous process) will also vary with the reaction conditions and desired yield, but is generally about 1 to 72 hours. In some of the foregoing embodiments, the reaction time or residence time is determined by the rate of conversion of the starting material. In some of the foregoing embodiments, the reaction mixture is reacted for 1 to 24 hours. In some of the foregoing embodiments, the reaction mixture is reacted for 1 to 10 hours. In some of the foregoing embodiments, the reaction mixture is reacted for 1 to 5 hours. In some of the foregoing embodiments, the reaction mixture is reacted for 1 to 3 hours. In some of the foregoing embodiments, the reaction mixture is reacted for less than 2 hours.

Isolation and Purification

The methods described herein may further include isolating the compound of formula I from the reaction mixture. In some embodiments, the methods described herein further includes isolating para-xylene from the reaction mixture. Any methods known in the art may be employed to isolate the product. For example, the compound of formula I (e.g., para-xylene) may be isolated by distillation.

In one exemplary embodiment, to isolate the compound of formula I (e.g., para-xylene) from the reaction mixture, the reaction mixture can be first filtered to remove any solid catalysts and desiccants (if present). The filtered mixture may then be transferred to a distillation column. One of skill in the art would know how to recover the compound of formula I (e.g., para-xylene) by distillation since the boiling points of the various components of the reaction mixture are known, including the boiling points of the solvents used. For example, in one embodiment where 1,4-dioxane is used, the solvent has a boiling point of 101° C. It is known in the art that para-xylene has a boiling point of 138° C.; HD has a boiling point of 191° C.; and DMF has a boiling point of 94° C. The solvent, HD, and/or DMF recovered can be recycled.

The methods described herein may also include purifying the isolated compound of formula I (e.g., para-xylene). Any suitable methods known in the art may be employed to purify the isolated compound of formula I (e.g., isolated para-xylene), including for example column chromatography or recrystallization.

Yield, Conversion and Selectivity

The yield of a product takes into account the conversion of the starting materials into the product, and the selectivity for the product over other byproducts that may be formed.

The difference between yield, conversion and selectivity is explained in the examples provided below. For example, with respect to the conversion of HD into para-xylene, the reaction can be generalized as follows, where "A" represents the moles of HD; "B" represents the moles of ethylene; "C" represents the moles of para-xylene; "D" represents the moles of water produced; and "a", "b", "c" and "d" are stoichiometric coefficients. With respect to the conversion of DMF into para-xylene, the reaction can be generalized as follows, where "A" represents the moles of DMF; "B" represents the moles of ethylene; "C" represents the moles of para-xylene; "D" represents the moles of water produced; and "a", "b", "c" and "d" are stoichiometric coefficients. For example, with respect to the conversion of HD and DMF into para-xylene, the reaction can be generalized as follows, where "A" represents the total moles of HD and DMF; "B" represents the moles of ethylene; "C" represents the mole of para-xylene; "D" represents the moles of water produced; and "a", "b", "c" and "d" are stoichiometric coefficients.

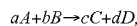

Conversion of A is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant A.

Selectivity is the stoichiometrically relative amount of product C produced from the converted amount of reactant A, as expressed as a percentage by the following equation:

$$\text{Selectivity (\%)} = \frac{Cf * \frac{a}{c}}{Ao - Af} * 100\%,$$

where $A_o$ is the starting moles of reactant A; $A_f$ is the final number of moles of reactant A; and $C_f$ is the number of moles of product C. In some embodiments where "a/c"=1, and the equation can be simplified to:

$$\text{Selectivity (\%)} = \frac{Cf}{Ao - Af} * 100.$$

The yield of product C is the percentage of reactant A that is converted into product C, as expressed by the following equation:

Yield (%)=Conversion (%)*Selectivity (%)

It should be understood that, when both DMF and HD are present, for example, selectivity is calculated based on the amount of the molar sum of DMF and HD.

In certain embodiments, the methods described herein have a yield of at least 10%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% to 100%, between 10% to 90%, between 20% to 80%, between 30% to 80%, between 40% to 80%, between 50%-80%, or between 60%-80% by weight.

In certain embodiments, the methods described herein have a selectivity of at least 10%, at least 20%, at least 30%, at least 40%, at least 50%, at least 60%, at least 70%, at least 80%, at least 90%, or at least 99%. In other embodiments, the selectivity is between 40% to 99%, between 40% to 95%, between 40% to 90%, between 40% to 80%, between 50% to 99%, between 50% to 95%, between 50% to 90%, between 50% to 80%, between 60% to 99%, between 60% to 95%, between 60% to 90%, between 60% to 80%, between 70% to 99%, between 70% to 95%, between 70% to 90%, or between 70% to 80%.

Downstream Products

The compounds of formula I, including para-xylene (PX or p-xylene) for example, produced according to the methods described herein may be suitable for manufacture of one or more plastics, solvents or fuels. As discussed above, para-xylene can also be further oxidized to produce terephthalic acid. The terephthalic acid can be further processed to manufacture one or more plastics.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−10%.

It should also be understood that reference to "between" two values or parameters herein includes (and describes) embodiments that include those two values or parameters per se. For example, description referring to "between x and y" includes description of "x" and "y" per se.

ENUMERATED EMBODIMENTS

The following enumerated embodiments are representative of some aspects of the invention.
1. A method for producing para-xylene, comprising:
   a) providing 2,5-hexanedione;
   b) providing ethylene;
   c) providing a catalyst;
   d) combining the 2,5-hexanedione, the ethylene, and the catalyst to form a reaction mixture; and
   e) producing para-xylene from at least a portion of the 2,5-hexanedione in the reaction mixture.
2. The method of embodiment 1, further comprising isolating para-xylene from the reaction mixture.
3. The method of embodiment 1, further comprising providing a solvent system, and combining the 2,5-hexanedione, the ethylene, the catalyst, and the solvent system to form the reaction mixture.
4. The method of embodiment 3, wherein the solvent system comprises an aprotic solvent.
5. The method of embodiment 3, wherein the solvent system comprises an ether solvent.
6. The method of embodiment 3, wherein the solvent system comprises a C1-C20 aliphatic solvent, a C6-C20 aromatic solvent, an alkyl phenyl solvent, a C2-C20 ether, a C2-C20 ester, a C1-C20 alcohol, a C2-C20 ketone, or any combinations or mixtures thereof.
7. The method of embodiment 3, wherein the solvent system comprises dimethylacetamide, acetonitrile, sulfolane, dioxane, dioxane, dimethyl ether, diethyl ether, glycol dimethyl ether (monoglyme), ethylene glycol diethyl ether (ethyl glyme), diethylene glycol dimethyl ether (diglyme), diethylene glycol diethyl ether (ethyl digylme), triethylene glycol dimethyl ether (triglyme), diethylene glycol dibutyl ether (butyl diglyme), tetraethylene glycol dimethyl ether (tetraglyme), polyglyme, proglyme, higlyme, tetrahydrofuran, ethylene glycol, diethylene glycol, triethylene glycol, polyethylene glycol, cyclobutanone, cyclopentanone, cyclohexanone, cycloheptanone, cyclooctanone, methyl acetate, ethyl acetate, propyl acetate, butyl acetate, methyl lactate, ethyl lactate, propyl lactate, butyl lactate, triacetin, dibutylphthalate, butane, pentane, cyclopentane, hexane, cyclohexane, heptane, cycloheptane, octane, cyclooctane, nonane, decane, undecane, dodecane, hexadecane, tetrachloride, chloroform, dichloromethane, nitromethane, toluene, anisole, nitrobenzene, bromobenzene, N-methylpyrrole, para-xylene, mesitylene, dodecylbenzene, pentylbenzene, hexylbenzene, Wibaryl® A, Wibaryl® B, Wibaryl® AB, Wibaryl® F, Wibaryl® R, Cepsa Petrepar® 550-Q, Santovac®, diphenyl ether, methyldiphenyl ether, ethyldiphenyl ether, water, or any combinations or mixtures thereof.
8. The method of embodiment 7, wherein the solvent system comprises dioxane, glyme, diglyme, triglyme, decane, dodecane, para-xylene, or any combinations or mixtures thereof.
9. The method of embodiment 8, wherein the solvent system comprises para-xylene.
10. The method of embodiment 1, wherein the catalyst comprises a Group 3 metal cation, a Group 9 metal cation, a Group 10 metal cation, a Group 11 metal cation, or a metal cation from the lanthanide series.
11. The method of embodiment 1, wherein the catalyst comprises a divalent metal cation or a trivalent metal cation.
12. The method of embodiment 1, wherein the catalyst comprises a metal cation selected from the group consisting of $Zn^{2+}$, $Cu^{2+}$, $Ni^{2+}$, $Co^{2+}$, $Al^{3+}$, $In^{3+}$, $Fe^{3+}$, $La^{3+}$, $Gd^{3+}$, and $Y^{3+}$.
13. The method of embodiment 1, wherein the catalyst is aluminum chloride, aluminum bromide, aluminum triflate, bismuth chloride, bismuth bromide, bismuth triflate, copper chloride, copper bromide, copper triflate, cobalt chloride, cobalt bromide, cobalt triflate, chromium chloride, chromium bromide, chromium triflate, iron chloride, iron bromide, iron triflate, gadolinium chloride, gadolinium bromide, gadolinium triflate, indium chloride, indium bromide, indium triflate, nickel chloride, nickel bromide, nickel triflate, neodymium chloride, neodymium bromide, neodymium triflate, magnesium chloride, magnesium bromide, magnesium triflate, lanthanum chloride, lanthanum bromide, lanthanum triflate, scandium chloride, scandium bromide, scandium triflate, tin chloride, tin bromide, tin triflate, titanium chloride, titanium bromide, titanium triflate, vanadium chloride, vanadium bromide, vanadium triflate, yttrium chloride, yttrium bromide, yttrium triflate, zinc chloride, zinc bromide, zinc triflate, copper acetate, copper acetylacetonate, or any combinations thereof.
14. The method of embodiment 13, wherein the catalyst is copper chloride, copper triflate, or yttrium triflate.
15. The method of embodiment 1, wherein the catalyst is a heteropolyacid.
16. The method of embodiment 1, wherein the catalyst is $\eta^2$-ethylene-copper(II)triflate.
17. The method of embodiment 1, wherein the catalyst is a metal chloride, metal triflate, metal acetate or metal acetylacetonate; and the solvent system comprises an ether, a $C_{8+}$ alkyl solvent, or para-xylene.
18. The method of embodiment 1, wherein the catalyst is copper chloride, copper triflate, or yttrium triflate; and the solvent system comprises dioxane, dodecane, para-xylene, or any mixtures or combinations thereof.
19. The method of embodiment 1, wherein at least a portion of the 2,5-hexanedione is converted to para-xylene at a temperature of at least 150° C.
20. The method of embodiment 19, wherein at least a portion of the 2,5-hexanedione is converted to para-xylene at a temperature of between 150° C. and 300° C.
21. A method for producing terephthalic acid, comprising:
   a) providing 2,5-hexanedione;
   b) providing ethylene;
   c) providing a catalyst;
   d) combining the 2,5-hexanedione, the ethylene, and the catalyst to form a reaction mixture; and
   e) producing para-xylene from at least a portion of the 2,5-hexanedione in the reaction mixture; and
   f) oxidizing the para-xylene to produce terephthalic acid.
22. The method of embodiment 21, further comprising isolating the 2,5-hexanedione produced in step (e) before oxidizing to produce terephthalic acid.

23. A method for producing one or more compounds of formula I:

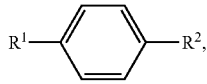

wherein each $R^1$ and $R^2$ is independently hydrogen, alkyl, cycloalkyl, heterocycloalkyl, aryl, or heteroaryl, comprising:

a) combining one or more compounds of formula A, one or more compounds of formula B:

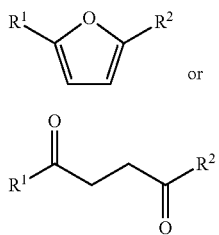

or any combinations thereof, with (i) ethylene and (ii) a sulfonic acid, or a salt, ester, anhydride or resin thereof, a sulfonamide, or a salt thereof, or a sulfonimide, or a salt thereof, to form a reaction mixture; and b) producing one or more compounds of formula I from at least a portion of the one or more compounds of formula A, the one or more compounds of formula B, or any combinations thereof, and at least a portion of the ethylene in the reaction mixture.

24. The method of embodiment 23, wherein the sulfonic acid, or the salt, ester, anhydride or resin thereof, the sulfonamide, or the salt thereof, or the sulfonimide, or the salt thereof, is formed in situ.

25. The method of embodiment 23 or 24, wherein the compound of formula A, the compound of formula B, or any combination thereof, is combined with (i) ethylene and (ii) a sulfonic acid, or a salt, ester, anhydride or polymer thereof.

26. The method of embodiment 25, wherein the sulfonic acid has a structure of formula $R^xSO_3H$, wherein $R^x$ is alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 8 substituents independently selected from the group consisting alkyl, haloalkyl, cycloalkyl, heterocycloalkyl, aryl, heteroaryl, nitro, —OR', —C(O)OR', —C(O)NR'R"—CHO, —COR', and cyano, wherein each R' and R" is independently hydrogen, alkyl, or haloalkyl.

27. The method of embodiment 26, wherein $R^x$ is alkyl, haloalkyl, or aryl optionally substituted with alkyl, haloalkyl, or nitro.

28. The method of embodiment 25, wherein the sulfonic acid is $CF_3SO_3H$ (i.e., triflic acid), $HCF_2CF_2SO_3H$, $C_6F_5SO_3H$, 4-methylbenzenesulfonic acid (i.e., p-toluene-sulfonic acid), or 2,4-dinitrobenzenesulfonic acid.

29. The method of embodiment 25, wherein the salt of the sulfonic acid has a structure of formula $Q^{r+}[R^xSO_3^-]_r$, wherein:

Q is a cation, $R^x$ is alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 5 substituents independently selected from the group consisting alkyl, haloalkyl, cycloalkyl, heterocycloalkyl, aryl, heteroaryl, nitro, —C(O)OR', —C(O)NR'R"—CHO, —COR', or cyano, wherein each R' and R" is independently hydrogen or alkyl; and and r is the charge of the cation.

30. The method of embodiment [0108], wherein $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

31. The method of embodiment [0108], wherein $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $NH_4^+$, $Sn^{4+}$, $Sn^{3+}$, $Sn^{2+}$, or $B^{3+}$.

32. The method of embodiment [0108], wherein $Q^{r+}$ is $Al^{3+}$, $Cu^{2+}$, $Cu^+$, $Gd^{3+}$, $In^{3+}$, $Ni^{2+}$, $Nd^{3+}$, $La^{3+}$, $Sc^{3+}$, $Y^{3+}$, $Zn^{2+}$, or $Co^{2+}$.

33. The method of embodiment [0108], wherein $Q^{r+}$ is $Cu^{2+}$, cut, $Gd^{3+}$, $In^{3+}$, $Nd^{3+}$, $La^{3+}$, $Sc^{3+}$, or $Y^{3+}$.

34. The method of embodiment [0108], wherein the salt of the sulfonic acid is $Al(OTf)_3$, $Bi(OTf)_3$, $Cu(OTf)_2$, $Cu(OTf)$, $Cr(OTf)_3$, $Fe(OTf)_3$, $Gd(OTf)_3$, $In(OTf)_3$, $Ni(OTf)_2$, $Nd(OTf)_3$, $Rb(OTf)$, $Cs(OTf)$, $Mg(OTf)_2$, $La(OTf)_3$, $Sc(OTf)_3$, $Ti(OTf)_4$, $V(OTf)_5$, $Y(OTf)_3$, $Zn(OTf)_2$, $Pt(OTf)_2$, $Pd(OTf)_2$, $AgOTf$, $Au(OTf)_3$, $Tl(OTf)_3$, $Tl(OTf)$, $Re(OTf)_3$, $Hg_2(OTf)_2$, $Hg(OTf)_2$, $NH_4(OTf)$, $Sn(OTf)_4$, $Sn(OTf)_3$, $Sn(OTf)_2$, $B(OTf)_3$, $Ga(OTf)_3$, $Pb(OTf)_4$, $Pb(OTf)_2$, $Co(OTf)_3$, $Co(OTf)_2$, $Ge(OTf)_4$, $Ge(OTf)_3$, $Ge(OTf)_2$, $Ge(OTf)$, $Ce(OTf)_4$, $Ce(OTf)_3$, or any combinations thereof.

35. The method of embodiment [0109], wherein the salt of the sulfonic acid is $Al(OTf)_3$, $Bi(OTf)_3$, $Cu(OTf)_2$, $Cu(OTf)$, $Cr(OTf)_3$, $Fe(OTf)_3$, $Gd(OTf)_3$, $In(OTf)_3$, $Ni(OTf)_2$, $Nd(OTf)_3$, $Mg(OTf)_2$, $La(OTf)_3$, $Sc(OTf)_3$, $Ti(OTf)_4$, $V(OTf)_5$, $Y(OTf)_3$, $Zn(OTf)_2$, $Pt(OTf)_2$, $Pd(OTf)_2$, $Ag(OTf)$, $Au(OTf)_3$, $NH_4(OTf)$, $Sn(OTf)_4$, $Sn(OTf)_3$, $Sn(OTf)_2$, $B(OTf)_3$, or any combinations thereof.

36. The method of embodiment [0109], wherein the salt of the sulfonic acid is $Al(OTf)_3$, $Cu(OTf)_2$, $Cu(OTf)$, $Gd(OTf)_3$, $In(OTf)_3$, $Ni(OTf)_2$, $Nd(OTf)_3$, $La(OTf)_3$, $Sc(OTf)_3$, $Y(OTf)_3$, $Zn(OTf)_2$, or $Co(OTf)_2$, or any combinations thereof.

37. The method of embodiment [0109], wherein the salt of the sulfonic acid is $Cu(OTf)_2$, $Cu(OTf)$, $Gd(OTf)_3$, $In(OTf)_3$, $Nd(OTf)_3$, $La(OTf)_3$, $Sc(OTf)_3$, $Y(OTf)_3$, or any combinations thereof.

38. The method of embodiment 25, wherein the compound of formula A, the compound of formula B, or any combination thereof, is combined with (i) ethylene and (ii) a sulfonic acid resin.

39. The method of embodiment 38, wherein the sulfonic acid resin is a halosulfonic acid resin.

40. The method of embodiment [0111], wherein the sulfonic acid resin is a fluorosulfonic acid resin.

41. The method of embodiment [0111], wherein the sulfonic acid resin is $R^{x1}CF_2SO_3H$, where $R^{x1}$ is alkyl or haloalkyl.

42. The method of embodiment 25, wherein the compound of formula A, the compound of formula B, or any combination thereof, is combined with (i) ethylene and (ii) a sulfonimide, or a salt thereof.

43. The method of embodiment 42, wherein the sulfonimide has a structure of formula $(R^{y1}SO_2)NH(SO_2R^{y2})$, wherein $R^{y1}$ and $R^{y2}$ are each independently alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 5 substituents independently selected from the group consisting alkyl, haloalkyl, cycloalkyl, heterocycloalkyl, aryl, and heteroaryl.

44. The method of embodiment 43, wherein the sulfonimide is $NH(Tf)_2$ (i.e., triflimide).

45. The method of embodiment 42, wherein the salt of the sulfonimide has a structure of formula $Q^{r+}[(R^{y1}SO_2)N(R^{y2}SO_2)]_r$, wherein:

Q is a cation, each $R^{y1}$ and $R^{y2}$ is independently alkyl, haloalkyl, cycloalkyl, heterocycloalkyl, aryl, or heteroaryl, wherein each alkyl, haloalkyl, cycloalkyl, heterocycloalkyl, aryl, or heteroaryl is optionally substituted with 1 to 5 substituents independently selected from the group consisting alkyl, haloalkyl, cycloalkyl, heterocycloalkyl, aryl, heteroaryl, nitro, —C(O)OR', —C(O)NR'R"—CHO, —COR', or cyano, wherein each R' and R" is independently hydrogen or alkyl; and and r is the charge of the cation.

46. The method of embodiment 45, wherein $Q^{r+}$+ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $Co^{3+}$, $Co^{2+}$, $Ge^{4+}$, $Ge^{2+}$, $Ce^{4+}$, or $Ce^{3+}$.

47. The method of embodiment 46, wherein $Q^{r+}$ is $Al^{3+}$, $Bi^{3\pm}$, $Cu^{2+}$, $Cu^+$, Cr', $Fe^{3+}$, $Gd^{3+}$, $In^{3+}$, $Ni^{3+}$, $Nd^{3+}$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, Pd', $Ag^+$, $Au^{3+}$, $NH_4^+$, $Sn^{4+}$, $Sn^{3+}$, $Sn^{2+}$, or $B^{3+}$.

48. The method of embodiment 46, wherein $Q^{r+}$ is $Al^{3+}$, $Cu^{2+}$, $Cu^+$, $Gd^{3+}$, $In^{3+}$, $Ni^{2+}$, $Nd^{3+}$, $La^{3+}$, $Sc^{3+}$, $Y^{3+}$, $Zn^{2+}$, or $Co^{2+}$.

49. The method of embodiment 46, wherein $Q^{r+}$ is $Cu^{2+}$, $Cu^+$, $Gd^{3+}$, $In^{3+}$, $Nd^{3+}$, $La^{3+}$, $Sc^{3\pm}$, or $Y^{3+}$.

50. The method of embodiment 45, wherein the salt of the sulfonimide is $Al[N(Tf)_2]_3$, $Bi[N(Tf)_2]_3$, $Cu[N(Tf)_2]_2$, $Cu[N(Tf)_2]$, $Cr[N(Tf)_2]_3$, $Fe[N(Tf)_2]_3$, $Gd[N(Tf)_2]_3$, $In[N(Tf)_2]_3$, $Ni[N(Tf)_2]_2$, $Nd[N(Tf)_2]_3$, $Li[N(Tf)_2]$, $Na[N(Tf)_2]$, $K[N(Tf)_2]$, $Rb[N(Tf)_2]$, $Cs[N(Tf)_2]$, $Mg[N(Tf)_2]_2$, $Ba[N(Tf)_2]_2$, $Ca[N(Tf)_2]_2$, $La[N(Tf)_2]_3$, $Sc[N(Tf)_2]_3$, $Ti[N(Tf)_2]_4$, $V[N(Tf)_2]_5$, $Y[N(Tf)_2]_3$, $Zn[N(Tf)_2]_2$, $Pt[N(Tf)_2]_2$, $Pd[N(Tf)_2]_2$, $Ag[N(Tf)_2]$, $Ag[N(Tf)_2]_2$, $Au[N(Tf)_2]_3$, $Tl[N(Tf)_2]_3$, $Tl[N(Tf)_2]$, $Re[N(Tf)_2]_3$, $Hg_2[N(Tf)_2]_2$, $Hg[N(Tf)_2]_2$, $NH_4[N(Tf)_2]$, $Sn[N(Tf)_2]_4$, $Sn[N(Tf)_2]_3$, $Sn[N(Tf)_2]_2$, $B[N(Tf)_2]_3$, $Ga[N(Tf)_2]_3$, $Pb[N(Tf)_2]_4$, $Pb[N(Tf)_2]_2$, $Co[N(Tf)_2]_3$, $Co[N(Tf)_2]_2$, $Ge[N(Tf)_2]_4$, $Ge[N(Tf)_2]_3$, $Ge[N(Tf)_2]_2$, $Ge[N(Tf)_2]$, $Ce[N(Tf)_2]_4$, $Ce[N(Tf)_2]_3$, or any combinations thereof.

51. The method of embodiment 45, wherein the salt of the sulfonimide is $Al[N(Tf)_2]_3$, $Bi[N(Tf)_2]_3$, $Cu[N(Tf)_2]_2$, $Cu[N(Tf)_2]$, $Cr[N(Tf)_2]_3$, $Fe[N(Tf)_2]_3$, $Gd[N(Tf)_2]_3$, $In[N(Tf)_2]_3$, $Ni[N(Tf)_2]_2$, $Nd[N(Tf)_2]_3$, $Mg[N(Tf)_2]_2$, $Ba[N(Tf)_2]_2$, $Ca[N(Tf)_2]_2$, $La[N(Tf)_2]_3$, $Sc[N(Tf)_2]_3$, $Ti[N(Tf)_2]_4$, $V[N(Tf)_2]_5$, $Y[N(Tf)_2]_3$, $Zn[N(Tf)_2]_2$, $Pt[N(Tf)_2]_2$, $Pd[N(Tf)_2]_2$, $Ag[N(Tf)_2]$, $Ag[N(Tf)_2]_2$, $Au[N(Tf)_2]_3$, $NH_4[N(Tf)_2]$, $Sn[N(Tf)_2]_4$, $Sn[N(Tf)_2]_3$, $Sn[N(Tf)_2]_2$, $B[N(Tf)_2]_3$, or any combinations thereof.

52. The method of embodiment 45, wherein the salt of the sulfonimide is $Al[N(Tf)_2]_3$, $Cu[N(Tf)_2]_2$, $Cu[N(Tf)_2]$, $Gd[N(Tf)_2]_3$, $In[N(Tf)_2]_3$, $Ni[N(Tf)_2]_2$, $Na[(Tf)_2]_3$, $La[N(Tf)_2]_3$, $Sc[N(Tf)_2]_3$, $Y[N(Tf)_2]_3$, $Zn[N(Tf)_2]_2$, or $Co[N(Tf)_2]_2$, or any combinations thereof.

53. The method of embodiment 45, wherein the salt of the sulfonimide is $Cu[N(Tf)_2]_2$, $Cu[N(Tf)_2]$, $Gd[N(Tf)_2]_3$, $In[N(Tf)_2]_3$, $Nd[N(Tf)_2]_3$, $La[N(Tf)_2]_3$, $Sc[N(Tf)_2]_3$, $Y[N(Tf)_2]_3$, or any combinations thereof.

54. The method of embodiment 42, wherein the salt of the sulfonimide is ethyldimethylpropylammonium bis(trifluoromethylsulfonyl)imide, 1-butyl-1-methylpyrrolidinium bis(trifluoromethylsulfonyl)imide, 1-ethyl-3-methylimidazolium bis(trifluoromethylsulfonyl)imide, 1-butyl-3-methylimidazolium bis(trifluoromethylsulfonyl)imide, 1-allyl-3-methylimidazolium bis(trifluoromethylsulfonyl)imide, triethylsulfonium bis(trifluoromethylsulfonyl)imide, or any combinations thereof.

55. The method of embodiment 23, wherein the sulfonic acid, or a salt, ester, anhydride or resin thereof, the sulfonamide, or a salt thereof, or the sulfonimide, or a salt thereof, is trihexyltetradecylphosphonium bis(trifluoromethylsulfonyl)amide, 1,2-dimethyl-3-propylimidazolium bis(trifluoromethylsulfonyl)imide, $[(C_6H_{13})_3(C_{14}H_{29})P]^+[(CF_3SO_2)_2N]^-$, $[C_{11}H_{16}N]^+[N(SO_2CF_3)_2]$, $[C_8H_{15}N_2]^+[N(SO_2CF_3)_2]$, $[C_6H_{11}N_2]^+[N(SO_2CF_2CF_3)_2]$, $[C_6H_{11}N_2]^+[N(SO_2CF_3)_2]$, $[C_6H_{14}N]^+[N(SO_2CF_3)_2]$, 1-butyl-1-methylpyrrolidinium trifluoromethanesulfonate, 1-ethyl-3-methylimidazolium trifluoromethanesulfonate, 1-butyl-3-methylimidazolium trifluoromethanesulfonate, 1-butyl-3-methylimidazolium trifluoromethanesulfonate, or any combinations thereof.

56. The method of embodiment 23, wherein the salt of the sulfonic acid, sulfonamide, or sulfonimide has a cation, wherein the cation has a standard reduction potential greater than −0.2 eV relative to standard hydrogen potential.

57. A method for producing one or more compounds of formula I:

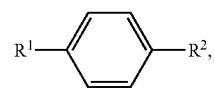

(I)

wherein each $R^1$ and $R^2$ is independently hydrogen, alkyl, cycloalkyl, heterocycloalkyl, aryl, or heteroaryl, comprising:

a) combining one or more compounds of formula A, one or more compounds of formula B:

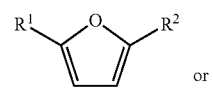

(A)

or

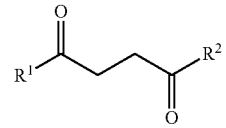

(B)

or any combinations thereof, with ethylene and a catalyst comprising a monovalent metal cation to form a reaction mixture, b) producing one or more compounds of formula I from at least a portion of the one or more compounds of formula A, the one or more compounds of formula B, or any combinations thereof, and at least a portion of the ethylene in the reaction mixture.

58. The method of embodiment 57, wherein the monovalent metal cation is Cu$^+$.

59. The method of embodiment 57, wherein the catalyst is Cu[(BF$_4$)(CH$_3$CN)$_4$], [Cu(OTf)]$_2$C$_6$H$_6$, or [Cu(OTf)](CH$_3$CN)$_4$.

60. A method for producing one or more compounds of formula I:

(I)

wherein each R$^1$ and R$^2$ is independently hydrogen, alkyl, cycloalkyl, heterocycloalkyl, aryl, or heteroaryl, comprising:

a) combining one or more compounds of formula A, one or more compounds of formula B:

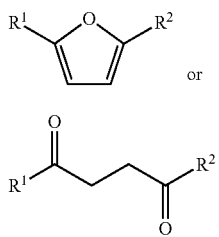
(A)

or (B)

or any combination thereof, with ethylene and an acid having a pKa that is lower than the pKa of sulfuric acid, b) producing one or more compounds of formula I from at least a portion of the one or more compounds of formula A, the one or more compounds of formula B, or any combination thereof, and at least a portion of ethylene, in the reaction mixture.

61. A method for producing one or more compounds of formula I:

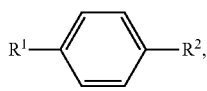
(I)

wherein each R$^1$ and R$^2$ is independently hydrogen, alkyl, cycloalkyl, heterocycloalkyl, aryl, or heteroaryl, comprising:

a) combining one or more compounds of formula A, one or more compounds of formula B:

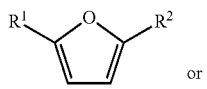
(A)

or

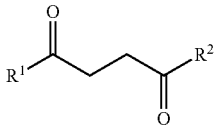
(B)

or any combinations thereof, with ethylene and a heteropolyacid, b) producing one or more compounds of formula I from at least a portion of the one or more compound of formula A, the one or more compounds of formula B, or any combinations thereof, in the reaction mixture.

62. The method of any one of embodiments 23 to 61, wherein R$^1$ and R$^2$ are each alkyl.

63. The method of embodiment 62, wherein R$^1$ and R$^2$ are each methyl.

64. The method of any one of embodiments 23 to 63, further comprising combining the one or more compounds of formula A, the one or more compounds of formula B, or any combination thereof, with a solvent system.

65. The method of embodiment 64, wherein the solvent system comprises an aliphatic solvent, an aromatic solvent, an alkyl phenyl solvent, an ether solvent, an ester solvent, an alcohol solvent, a ketone solvent, an ionic liquid, or any combinations or mixtures thereof.

66. The method of embodiment 65, wherein the solvent system comprises an alkyl solvent, or a polyphenyl ether.

67. The method of embodiment 65, wherein the solvent system comprises dimethylacetamide, acetonitrile, sulfolane, dioxane, dioxane, dimethyl ether, diethyl ether, glycol dimethyl ether (monoglyme), ethylene glycol diethyl ether (ethyl glyme), diethylene glycol dimethyl ether (diglyme), diethylene glycol diethyl ether (ethyl digylme), triethylene glycol dimethyl ether (triglyme), diethylene glycol dibutyl ether (butyl diglyme), tetraethylene glycol dimethyl ether (tetraglyme), polyglyme, proglyme, higlyme, tetrahydrofuran, ethylene glycol, diethylene glycol, triethylene glycol, polyethylene glycol, cyclobutanone, cyclopentanone, cyclohexanone, cycloheptanone, cyclooctanone, methyl acetate, ethyl acetate, propyl acetate, butyl acetate, methyl lactate, ethyl lactate, propyl lactate, butyl lactate, triacetin, dibutylphthalate, butane, pentane, cyclopentane, hexane, cyclohexane, heptane, cycloheptane, octane, cyclooctane, nonane, decane, undecane, dodecane, hexadecane, tetrachloride, chloroform, dichloromethane, nitromethane, toluene, anisole, nitrobenzene, bromobenzene, methylpyrrole, methylpyrrolidinone, dimethylfuran, dichlorobenzene, water, paraxylene, mesitylene, dodecylbenzene, pentylbenzene, hexylbenzene, Wibaryl® A, Wibaryl® B, Wibaryl® AB, Wibaryl® F, Wibaryl® R, Cepsa Petrepar® 550-Q, Santovac®, diphenyl ether, methyldiphenyl ether, ethyldiphenyl ether, water, or any combinations or mixtures thereof.

68. The method of embodiment 23, wherein:
R$^1$ and R$^2$ are each methyl; or R$^1$ is methyl and R$^2$ is hydrogen; and
a sulfonic acid, or a salt, ester, anhydride or polymer thereof.

69. The method of embodiment 23, wherein:
R$^1$ and R$^2$ are each methyl; and
a sulfonic acid, or a salt, ester, anhydride or polymer thereof.

70. The method of embodiment 69 or 69, wherein:
the sulfonic acid or a salt thereof is triflic acid or a salt thereof.

71. The method of embodiment 64, wherein the solvent system comprises para-xylene.

72. The method of embodiment 64, wherein the solvent system comprises a C4-C30 alkyl solvent.
73. The method of embodiment 72, wherein the C4-C30 alkyl solvent is branched.
74. The method of embodiment 64, wherein:
   $R^1$ and $R^2$ are each methyl; or $R^1$ is methyl and $R^2$ is hydrogen; and
   the solvent system comprises para-xylene, a C4-C30 alkyl solvent, or any mixture thereof.
75. The method of embodiment 64, wherein:
   $R^1$ and $R^2$ are each methyl; and
   the solvent system comprises para-xylene, a C4-C30 alkyl solvent, or any mixture thereof.

EXAMPLES

The following Examples are merely illustrative and are not meant to limit any aspects of the present disclosure in any way.

Example 1

Preparation of PX from DMF

A mixture of 5.0 g of DMF, 0.025 g of copper triflate, and 100 mL of dioxane were charged to a high pressure autoclave fitted with a gas entrainment impeller. The autoclave was purged 3 times with nitrogen, once with ethylene, and then pressurized to 500 psig (3,447 kpas) with ethylene. The autoclave was heated to 250° C. at which point the pressure increased to 2250 psig (15,513 kpas). The reactor remained pressurized at 250° C. for 7 hours whereby the heater was turned off and the reactor was allowed to cool at RT The pressure was vented and the reaction solution was decanted into a storage bottle. The reaction mixture was a light yellow solution with a slight amount of black precipitate. The solution phase was analyzed by $^1H$ and $^{13}C$ NMR spectroscopy, identifying residual DMF, PX, ethylene and HD as the major components together with dioxane as solvent. These components were quantified by $^1H$ NMR spectroscopy, the values being given in Table 1 below. Ethylene was observed in this sample at about 0.3 mole % by NMR.

The protocol in this Example was repeated for various catalysts, solvents and temperatures as specified in Table 1 below.

Example 2

Preparation of PX from DMF and HD

A mixture of 8.0 g of DMF, 2.0 g of HD, 0.5 g of yttrium triflate, and 200 g of dioxane were charged to a high pressure autoclave fitted with a gas entrainment impeller. The autoclave was purged 3 times with nitrogen, once with ethylene, and then pressurized to 500 psig (3,447 kpas) with ethylene. The autoclave was heated to 250° C. at which point the pressure increased to 2,000 psig (13,790 kpas). The reactor remained pressurized at 250° C. for 7 hours. Samples were taken at hour intervals and analyzed by NMR spectroscopy for conversion and selectivity. After 7 hours, the heater was turned off and the reactor was allowed to cool to RT. The pressure was vented and the reaction solution was decanted into a storage bottle. A conversion of 100% was obtained after 7 hours with a molar selectivity to PX based on HD and DMF of 90%, yield equal to 90%.

Example 3

Preparation of PX from HD

A mixture of 5.0 g of HD, 0.05 g of copper triflate, and 100 g of dioxane were charged to a high pressure autoclave fitted with a gas entrainment impeller. The autoclave was purged 3 times with nitrogen, once with ethylene, and then pressurized to 500 psig (3,447 kpas) with ethylene. The autoclave was heated to 250° C. at which point the pressure increased to 1900 psig (13,100 kpas). The reactor remained pressurized at 250° C. for 7 hours. Samples were taken at hour intervals and analyzed by NMR spectroscopy for conversion and selectivity. After 7 hours, the heater was turned off and the reactor was allowed to cool to RT. The pressure was vented and the reaction solution was decanted into a storage bottle. A conversion of 94% was obtained after 7 hours with a molar selectivity to PX based on HD of 99%, yield equal to 93%.

Example 4 (Comparative Example)

Comparison of PX Production From DMF Using Activated Carbon Versus Other Catalysts A mixture of 10.0 g of DMF, 1.0 g of Norit Darco G60 activated carbon, 2.1 g of 3 Å molecular sieves (predried),

TABLE 1

| Reaction Conditions | | | | Products | | | | | |
|---|---|---|---|---|---|---|---|---|---|
| Catalyst | Solvent | Temp (° C.) | DMF mol % | DMF mol % | PX mol % | HD mol % | Conversion % | Selectivity % | Yield % |
| Gd(OTf)$_3$ | Dioxane | 190 | 4.38 | 1.23 | 2.37 | 0.12 | 72 | 75 | 54 |
| In(OTf)$_3$ | Dioxane | 190 | 3.43 | 0.73 | 2.18 | 0.39 | 79 | 80 | 63.2 |
| AlCl$_3$ | Dioxane | 190 | 3.43 | 0.93 | 1.92 | 0.2 | 73 | 79 | 57.7 |
| AlCl$_3$ | Dioxane | 220 | 3.43 | 0.08 | 2.99 | 0.12 | 98 | 89 | 87.2 |
| Cu(OTf)$_2$ | Dioxane | 190 | 4.38 | 1.39 | 2.64 | 0.34 | 68 | 88 | 59.8 |
| InCl$_3$ | Dioxane | 190 | 4.38 | 1.17 | 2.42 | 1.4 | 73 | 75 | 54.8 |
| CuCl$_2$ | Dioxane | 190 | 4.38 | 1.57 | 2.45 | 4.6 | 64 | 87 | 55.7 |
| CuCl$_2$ | Dioxane | 220 | 4.38 | 0.02 | 3.99 | 3.8 | 99.5 | 91.6 | 91.1 |
| CuCl$_2$ | Dioxane | 250 | 4.38 | 0.28 | 3.94 | 1.73 | 91.8 | 98.0 | 90.0 |
| Cu(OTf)$_2$ | Dioxane | 220 | 4.38 | 0.04 | 4.16 | 1.8 | 99.1 | 95.9 | 95.0 |
| Cu(OTf)$_2$ | Dioxane | 250 | 4.38 | 0.04 | 4.32 | 0 | 98.9 | 99.6 | 98.5 |
| Y(OTf)$_3$ | Dioxane | 220 | 4.38 | 0.13 | 3.87 | 2.2 | 97 | 91.1 | 88.4 |
| Cu(OTf)$_2$ | Triglyme | 250 | 8.48 | 0 | 7.93 | 0 | 100 | 93.4 | 93.5 |

Mol % refers to mol % in dioxane, except for the HD which is calculated as the mol % of initial DMF and 200 g of dioxane were charged to a high pressure autoclave fitted with a gas entrainment impeller. The autoclave was purged 3 times with nitrogen, once with ethylene, and then pressurized to 460 psig (3,1712 kpas). The autoclave was heated to 190° C. at which point the pressure increased to 1270 psig (8,756 kpas). The reactor remained pressurized at 190° C. for 24 hours when the heater was turned off and the reactor was allowed to cool at RT. Prior to cooling, the pressure had decreased to 1240 psig (8,549 kpas). The pressure was vented and the reaction solution was decanted into a storage bottle. The reaction mixture was cloudy and black, but upon standing it clarified somewhat as the Norit settled. The solution was analyzed by $^1$H and $^{13}$C NMR spectroscopy, identifying residual DMF, PX, ethylene and HD as the major components together with dioxane as solvent. These components were quantified by $^1$H NMR spectroscopy, the values being given in Table A below. Very little conversion of DMF was observed, only 4.6%, and of that amount only 19% was converted to PX.

The protocol in this Comparative Example was repeated for various catalyst s, solvents and temperatures as specified in Table 2 below.

TABLE 2

| | Reaction Conditions | | | | Products | | | | |
|---|---|---|---|---|---|---|---|---|---|
| Catalyst | Solvent | Temp (° C.) | DMF mol % | DMF mol % | PX mol % | HD mol % | Conversion % | Selectivity % | Yield % |
| Norit Darco G60 | Dioxane | 190 | 4.38 | 4.18 | 0.04 | 0.05 | 4.6 | 19 | 0.9 |
| Cu(l)/Mordenite | Dioxane | 220 | 4.31 | 3.96 | 0.06 | 0.27 | 8 | 17.5 | 1.4 |
| NiCl$_2$ | Dioxane | 190 | 4.38 | 3.93 | 0.25 | 1 | 10 | 56 | 5.6 |
| Norit CA1 (H$_3$PO$_4$ Treated) | Dioxane | 220 | 4.308 | 3.9 | 0.35 | 0.9 | 11.1 | 73 | 8.1 |
| Norit CA1 | Dioxane | 220 | 4.38 | 3.7 | 0.49 | 1.5 | 15.7 | 71.6 | 11.2 |
| NiCl$_2$ | Dioxane | 190 | 4.38 | 3.93 | 0.25 | 1 | 10 | 56 | 5.6 |
| CoCl$_2$ | Dioxane | 190 | 4.38 | 2.61 | 1.34 | 9.1 | 40 | 76 | 30.4 |
| HY Zeolite | Dioxane | 190 | 5.42 | 2.38 | 1.5 | 0.37 | 56 | 49 | 27.4 |
| ZnCl$_2$ | Dioxane | 190 | 4.38 | 3.23 | 0.91 | ND | 26 | 79 | 20.5 |
| Y(OTf)$_3$ | Sulfolane | 250 | 5.88 | 0.70 | 2.13 | ND | 88.1 | 41.2 | 36.3 |
| Y(OTf)$_3$ | n-Methylpyrrolidone | 250 | 3.57 | 0.14 | 3.21 | 0.00 | 97.1 | 67.6 | 65.6 |
| Y(OTf)$_3$ | Dimethylsulfoxide | 250 | 3.76 | Solvent decomposed, pressure increased sharply, and reaction was stopped | | | | | |
| Y(OTf)$_3$ | Tetraethyleneglycol | 250 | 9.18 | 1.01 | 3.03 | 2.68 | 86.4 | 38.2 | 33.0 |
| Y(OTf)$_3$ | Propylene Carbonate | 250 | 4.85 | Solvent decomposed, pressure increased sharply, and reaction was stopped | | | | | |

Mol % refers to mol % in dioxane, except for the HD which is calculated as the mol % of initial DMF
ND refers to "no data"

Example 5

Comparison of Supported Versus Unsupported Catalysts

This example compares the rate of reaction in converting DMF into PX using supported catalysts (e.g., CuCl$_2$ on alumina, CuCl$_2$ on HY Zeolite) versus unsupported catalysts (e.g., CuCl$_2$, Cu(OTf)$_2$, Y(OTf)$_3$).

A mixture of 10 g of DMF, catalyst (type and amount as specified in Table 3 below), and 200 g of dioxane were charged to a high pressure autoclave fitted with a gas entrainment impeller. The autoclave was purged 3 times with nitrogen, once with ethylene, and then pressurized to 500 psig (3,447 kpas) with ethylene. The autoclave was heated to 250° C. The reactor remained pressurized at 250° C. for 7 hours. Samples were taken at hour intervals and analyzed by NMR spectroscopy for conversion and selectivity. After 7 hours, the heater was turned off and the reactor was allowed to cool to RT. The pressure was vented and the reaction solution was decanted into a storage bottle. Conversion, molar selectivity, and yield for each catalyst are summarized in Table 3 below.

TABLE 3

Summary of data (10 g DMF, 200 g Dioxane, 250° C., 500 psig C$_2$H$_4$)

| Catalyst | Amount of Catalyst (g) | Conversion after 7 hrs (mol %) | Selectivity (mol %) | HD (mol %) | Time to reach 50% conversion (hrs) | Yield (mol %) |
|---|---|---|---|---|---|---|
| CuCl$_2$ on Alumina | 2.0 | 52 | 70 | 1.3 | 6.7 | 36.4 |

TABLE 3-continued

Summary of data (10 g DMF, 200 g Dioxane, 250° C., 500 psig C₂H₄)

| Catalyst | Amount of Catalyst (g) | Conversion after 7 hrs (mol %) | Selectivity (mol %) | HD (mol %) | Time to reach 50% conversion (hrs) | Yield (mol %) |
|---|---|---|---|---|---|---|
| CuCl₂ on HY Zeolite | 2.0 | 77 | 82 | 1.3 | 2.6 | 63.1 |
| CuCl₂ | 1.0 | 97 | 91 | 0.6 | 1.1 | 88.3 |
| Cu(OTf)₂ | 0.5 | 100 | 86 | 0.0 | 1.3 | 86.0 |
| Y(OTf)₃ | 0.5 | 99 | 84 | 0.0 | 1.0 | 83.2 |

Based on the results of Table 3 above, the non-supported catalysts were observed to convert DMF into PX faster than the supported catalysts.

Example 6

Comparison of Types and Amounts of Different Catalysts

This example compares the rate of reaction in converting DMF into PX using varying amounts of catalyst.

The protocol described in Example 5 above for converting DMF into PX was used for three different catalysts (i.e., CuCl₂, Cu(OTf)₂, and Y(OTf)₃), according to the conditions set forth in Tables 4, 5, and 6 below, respectively. Conversion, molar selectivity, and yield for each catalyst are also summarized in each table below.

TABLE 4

Summary of CuCl₂ (10 g DMF, 200 g Dioxane, 250° C., 500 psig C₂H₄)

| Catalyst | Catalyst (g) | Conversion after 7 hrs (mol %) | Selectivity (mol %) | HD (mol %) | Time to reach 50% conversion (hrs) | Yield (mol %) |
|---|---|---|---|---|---|---|
| CuCl₂ | 0.10 | 70 | 101 | 3.2 | 3.5 | 70 |
| CuCl₂ (rerun) | 0.10 | 65 | 98 | 3.2 | 4.2 | 64 |
| CuCl₂ | 0.50 | 92 | 98 | 1.7 | 1.5 | 90 |
| CuCl₂ | 1.00 | 97 | 91 | 1.0 | 1.1 | 88 |

TABLE 5

Summary of Cu(OTf)₂ data (250° C., 500 psig C₂H₄)

| Catalyst | Catalyst (g) | DMF (g) | Dioxane (g) | Conversion after 7 hrs (mol %) | Selectivity (mol %) | HD (mol %) | Time to reach 50% conversion (hrs) | Yield (mol %) |
|---|---|---|---|---|---|---|---|---|
| Cu(OTf)₂ | 0.025 | 5 | 100 | 99 | 100 | 0.1 | 0.3 | 99 |
| Cu(OTf)₂ | 0.05 | 10 | 200 | 98 | 100 | 0.5 | 1.0 | 98 |
| Cu(OTf)₂ | 0.10 | 10 | 200 | 100 | 95 | 0.0 | 1.0 | 95 |
| Cu(OTf)₂ (rerun) | 0.10 | 10 | 200 | 99 | 101 | 0.1 | 1.2 | 100 |
| Cu(OTf)₂ | 0.50 | 10 | 200 | 100 | 86 | 0.0 | 1.3 | 86 |

TABLE 6

Summary of Y(OTf)₃ data (10 g DMF, 200 g Dioxane, 250° C., 500 psig C₂H₄)

| Catalyst | Catalyst (g) | Conversion after 7 hrs (mol %) | Selectivity (mol %) | HD (mol %) | Time to reach 50% conversion (hrs) | Yield (mol %) |
|---|---|---|---|---|---|---|
| Y(OTf)₃ | 0.50 | 99 | 84 | 0.0 | 1.1 | 84 |
| Y(OTf)₃ | 0.25 | 100 | 92 | 0.4 | 1.1 | 92 |
| Y(OTf)₃ | 0.10 | 98 | 94 | 0.4 | 1.3 | 92 |

Example 7

Comparison of Solvent Concentration

This examples compares the rate of reaction in converting DMF into PX using different concentrations of dioxane as the solvent.

The protocol described in Example 5 above for converting DMF into PX was used according to the conditions set forth in Table 7 below. The samples taken from the reaction phase were each separated. The phases observed were an upper, opaque, PX-rich phase, and a lower water/dioxane phase. Conversion, molar selectivity, and yield for each catalyst are also summarized in Table 7 below.

TABLE 7

Summary of solvent concentration data (0.5 g Y(OTf)$_3$, 200 g Dioxane, 250° C., 500 psig C$_2$H$_4$)

| Catalyst | DMF (g) | Conversion after 7 hrs (mol %) | Selectivity (mol %) | HD (mol %) | Time to reach 50% conversion (hrs) | Yield (mol %) |
|---|---|---|---|---|---|---|
| Y(OTf)$_3$ | 20 | 100 | 85 | 0.1 | 0.8 | 85 |
| Y(OTf)$_3$ | 10 | 99 | 84 | 0.0 | 1.1 | 83 |

Example 8

Comparison of Solvent Types

This examples compares the rate of reaction in converting DMF into PX using different solvents, including dioxane, triglyme, triethylene glycol (TEG), N-methylpyrrole (NMP), sulfolane, propylene carbonate, and dimethylsulfoxide (DMSO).

The protocol described in Example 5 above for converting DMF into PX was used according to the conditions set forth in Table 8 below. Conversion, molar selectivity, and yield for each catalyst for dioxane, TEG, sulfolane, triglyme and NMP are also summarized in Table 8 below. Propylene carbonate was observed to be unstable at 250° C. and appeared to have degraded into CO$_2$. Similarly, DMSO was also unstable at 250° C. and appeared to have degraded. As such, the reactions using propylene carbonate and DMSO were not sampled.

TABLE 8

Summary of solvent data (0.5 g Y(OTf)$_3$, 10 g DMF, 250° C., 500 psig C$_2$H$_4$)

| Solvent | Solvent (g) | Conversion after 7 hrs (mol %) | Selectivity (mol %) | HD (mol %) | Time to reach 50% conversion (hrs) | Yield (mol %) |
|---|---|---|---|---|---|---|
| Dioxane | 200 | 99 | 84 | 0.0 | 1.1 | 84 |
| TEG | 200 | 100 | 27 | 0.0 | <<1.0 | 27 |
| Sulfolane | 200 | 88 | 41 | 0.0 | ND | 36 |
| Triglyme | 200 | 99 | 81 | 0.0 | 0.9 | 81 |
| NMP | 200 | 97 | 68 | 0.0 | <<1.0 | 66 |

ND refers to "no data"

Based on the data in Table 8, dioxane and triglyme were observed to have similar reaction kinetics in converting DMF into PX. NMP was also observed to be a suitable solvent for converting DMF into PX.

Example 9

Comparison of Solvents for Improving PX Selectivity

This examples compares the rate of reaction in converting DMF into PX using different solvents and catalysts s. The solvents used include triglyme and triethylene glycol (TEG). The catalysts s include Cu(OTf)$_2$ and Y(OTf)$_3$.

The protocol described in Example 5 above for converting DMF into PX was used according to the conditions set forth in Tables 9 and 10 below. Conversion, molar selectivity, and yield for each catalyst for each solvent/catalyst combinations are summarized in the tables below.

TABLE 9

Summary of triglyme data (10 g DMF, 250° C., 500 psig C$_2$H$_4$)

| Catalyst | Catalyst (g) | Triglyme (g) | Conversion after 7 hrs (mol %) | Selectivity (mol %) | HD (mol %) | Time to reach 50% conversion (hrs) | Yield (mol %) |
|---|---|---|---|---|---|---|---|
| Cu(OTf)$_2$ | 0.05 | 200 | 100 | 94 | 0.0 | 1.1 | 94 |
| Y(OTf)$_3$ | 0.50 | 200 | 99 | 82 | 0.0 | 0.9 | 81 |

TABLE 10

Summary of TEG data (500 psig C$_2$H$_4$)

| Catalyst | Catalyst (g) | TEG (g) | DMF (g) | Temp (° C.) | Conversion after 7 hrs (mol %) | Selectivity (mol %) | HD (mol %) | Time to reach 50% conversion (hrs) | Yield (mol %) |
|---|---|---|---|---|---|---|---|---|---|
| Y(OTf)$_3$ | 0.05 | 100 | 5 | 220 | 86 | 38 | 3.0 | 1.0 | 33 |
| Y(OTf)$_3$ | 0.50 | 200 | 10 | 250 | 100 | 27 | 0.0 | <<1.0 | 27 |

Based on the data in Table 9 above, triglyme as the solvent and Cu(OTf)$_2$ as the catalyst showed comparable reaction kinetics in converting DMF to PX as dioxane as the solvent and Cu(OTf)$_2$ as the catalyst (based on the data in Table 5 of Example 6 above).

Example 10

Comparison of Temperature

This example compares the rate of reaction in converting DMF into PX at different temperatures. The protocol described in Example 5 above for converting DMF into PX was used according to the temperatures set forth in Table 11 below. The reactions in this example used 10 g DMF, 1.0 g CuCl$_2$, 200 g dioxane, and 500 psig C$_2$H$_4$. Conversion and molar selectivity, and yield are summarized in Table 11 below.

TABLE 11

Summary of temperature data (1.0 g CuCl$_2$, 10 g DMF, 200 g Dioxane, 500 psig C$_2$H$_4$)

| Temperature (° C.) | Conversion after 7 hrs (mol %) | Selectivity (mol %) | HD (mol %) | Time to reach 50% conversion (hrs) | Yield (mol %) |
|---|---|---|---|---|---|
| 180 | 22 | 72 | 5.5 | 23 | 16 |
| 250 | 96 | 91 | 1.0 | 1.2 | 88 |

Temperature was observed to have a effect on the kinetics of the reaction. For the reaction to take place with around 90% conversion in a reasonable amount of time, temperatures close to 250° C. should be used. Lowering the reaction temperature surprisingly did not increase selectivity, as selectivity was observed to increase with time and conversion in the 180° C. reaction at the end of 7 hours.

Example 11

Comparison of Pressure

This example compares the rate of reaction in converting DMF into PX at different pressures. The protocol described in Example 5 above for converting DMF into PX was used according to the conditions set forth in Tables 12 and 13 below. The solvent used in this example was dioxane, and the catalysts used were $CuCl_2$ and $Y(OTf)_3$. Conversion, molar selectivity, and yield for each catalyst for each catalyst/pressure combination is summarized in the tables below.

TABLE 12

Summary of $Y(OTf)_3$/pressure data (0.5 g $Y(OTf)_3$, 10 g DMF, 200 g dioxane, 250° C.

| Pressure (psig) | Conversion after 7 hrs (mol %) | Selectivity (mol %) | HD (mol %) | Time to reach 50% conversion (hrs) | Yield (mol %) |
|---|---|---|---|---|---|
| 300 | 97 | 87 | 0.5 | 1.6 | 85 |
| 500 | 99 | 84 | 0.0 | 1.0 | 83 |
| 550 | 100 | 90 | 0.0 | 1.0 | 90 |

TABLE 13

Summary of $CuCl_2$/pressure data (1.0 g $CuCl_2$, 10 g DMF, 200 g dioxane, 180° C.)

| Pressure (psig) | Conversion after 7 hrs (mol %) | Selectivity (mol %) | HD (mol %) | Time to reach 50% conversion (hrs) | Yield (mol %) |
|---|---|---|---|---|---|
| 500 | 22 | 72 | 5.5 | 23 | 16 |
| 700 | 33 | 64 | 2.7 | 11 | 21 |

Example 12

PX Production From HD

This example demonstrates the conversion of HD into PX. The protocol described in Example 5 was used in for HD (2 g) as the starting material. $Y(OTf)_3$ (0.5 g) was used as the catalyst, dioxane (200 g) as the solvent. Ethylene was provided at 500 psig, and the reaction temperature was 250° C. Conversion, molar selectivity, and yield are summarized Table 14 below.

TABLE 14

Summary of HD data

| Catalyst | Conversion after 7 hrs (mol %) | Selectivity (mol %) | HD (mol %) | Time to reach 50% conversion (hrs) | Yield (mol %) |
|---|---|---|---|---|---|
| $Y(OTf)_3$ | 100 | 90 | 0.0 | 0.9 | 90 |

Based on the data in Table 14 above, HD was observed convert into PX with a selectivity of about 99% was observed for $Y(OTf)_3$ as the catalyst.

As a control, a reaction using HD with no ethylene or catalyst (5 g HD, 100 g dioxane, 250° C.) was performed. HD was not observed to convert to DMF without the presence of a catalyst. Additionally, HD with a catalyst but no ethylene (5 g HD, 0.25 g $Y(OTf)_3$, 100 g Dioxane, 250° C.) was also performed. After 1 hour of reaction time, 86% of HD was converted with 62% selectivity to DMF.

Example 13

Comparison Using Heteropolyacids

This example compares the rate of reaction in converting DMF into PX using heteropolyacid catalysts. The protocol described in Example 5 was used in for each catalyst and solvent along with the reaction conditions as summarized in Table 15 below. PX yield for each reaction is also provided in Table 15 below.

TABLE 15

Summary of HPAs data (10 g DMF, 0.5 g catalyst, 200 g solvent, 250° C., 500 psig $C_2H_4$)

| Catalyst | Solvent | Conversion after 7 hrs (mol %) | Selectivity (mol %) | Yield (mol %) |
|---|---|---|---|---|
| 12-molybdosilicic acid hydrate | Dioxane | 98.8 | 84.8 | 83.8 |
| $[MoO_3][H_3PO_4] \cdot H_2O$ | Dioxane | 97.9 | 84.8 | 77.1 |
| 12-molybdosilicic acid | Triglyme | n/a | n/a | ND |

ND = NMR spectrum was not run

Example 14

Comparison Using Various Solvents

This example compares the rate of reaction in converting DMF into PX using aliphatic solvents, and mixtures of solvents. The protocol described in Example 5 was used in for each catalyst and solvent along with the reaction conditions as summarized in Tables 16 below and 17. PX yield for each reaction is also provided in Tables 16 and 17 below.

TABLE 16

Summary of solvent data (10 g DMF, 0.5 g catalyst, 200 g solvent, 250° C., 500 psig $C_2H_4$)

| Catalyst | Solvent | Conversion after 7 hrs (mol %) | Selectivity (mol %) | Yield (mol %) |
|---|---|---|---|---|
| Cu (II) bis(trifluoromethylsulfonyl)imide | Dioxane | 98.6 | 96.0 | 94.7 |
| $Cu(OTf)_2$ | Dioxane | 100.0 | 85.8 | 85.8 |
| $Cu(OTf)_2$ | Water | n/a | n/a | Phase separated and not quantified |
| $Cu(OTf)_2$ | Dodecane | 92.1 | 85.9 | 79.1 |
| $Cu(OTf)_2$ | Dioxane + Dodecane | 99.4 | 92.2 | 91.6 |

TABLE 17

Summary of aliphatic solvent data

| Catalyst | Catalyst (g) | DMF (g) | Solvent | Solvent (g) | Temp (° C.) | Pressure (psi) | Conversion (molar) | Selectivity (molar) |
|---|---|---|---|---|---|---|---|---|
| Cu(OTf)$_2$ | 0.1 | 30.01 | n-Heptane Dioxane | 60.01 0.1 | 200 | 2100 | 74.1 | ND |
| Cu(OTf)$_2$ | 2.51 | 20.01 | Dodecane | 30.01 | 250 | 1550-1575 | 99.7 | 52.4 |
| Cu(OTf)$_2$ | 0.1 | 30.01 | Decane | 60.01 | 250 | 2275-1900 | 94.6 | 98.4 |
| Cu(OTf)$_2$ | 0.15 | 21.0 | Dodecane | 30.01 | 250 | 650 | 93.0 | 101.9 |
| Cu(OTf)$_2$ | 0.15 | 20.0 | Dodecane Dioxane | 30.00 0.1 | 250 | 800 | 93.4 | 102.7 |

ND = quantification of selectivity not available, but PX was observed as a product Example 15

Comparison Using Copper-Containing Salt Catalysts

This example compares the rate of reaction in converting DMF into PX using metal-containing salt catalysts, such as copper acetate and copper acetylacetonate. The protocol described in Example 5 was used in for each catalyst and solvent along with the reaction conditions as summarized in Table 18 below. PX yield for each reaction is also provided in Table 18 below.

TABLE 18

Summary of copper-containing salt catalyst data (2.5 g DMF, 50 g dioxane, 0.125 g catalyst, 250° C., 1500-1600 psig C$_2$H$_4$)

| Copper-containing salt catalyst | Conversion (molar) | Selectivity (molar) |
|---|---|---|
| copper acetate | 85.9 | ND |
| copper acetylacetonate | 80.1 | 94.5 |

ND = quantification of selectivity not available, but PX was observed as a product Example 16

Comparison of Solvents

This example compares the effect of various solvents in converting DMF into PX using Cu(OTf)$_2$ as the catalyst.

DMF and the catalyst specified in Table 16 below were charged in the Parr vessel and the reactor was sealed, placed in the heating mantle and attached to the nitrogen line, ethylene cylinder, temperature controller and a waste container (through the gas release valve). The reaction mixture was flushed three times with nitrogen (nitrogen pressure of about 80 psig) and three times with ethylene (ethylene pressure of about 100 psig) then 500 psig ethylene was introduced in the reaction mixture and the mixture stirred. The ethylene pressure dropped with stirring to a certain value (depending on the solvent used) where it stabilized. The pressure was readjusted to 500 psig by adding more ethylene. The reaction mixture was heated to 250° C. and maintained at this temperature for 7 hours. At the end of the reaction time, the heating mantle was removed and the Parr reactor was subjected to a nitrogen flow to enable cooling. Once the reactor was brought to room temperature the excess ethylene was slowly released through the gas release valve and the reaction mixture was transferred in a sample container and submitted to analysis by NMR and GC-MS. PX conversion and selectivity for each reaction is also provided in Table 19 below.

TABLE 19

Summary of solvent screen data

| Solvent | DMF (g) | Solvent (g) | Cu(OTf)$_2$ (g) | Conversion (%) | Selectivity (%) |
|---|---|---|---|---|---|
| Cyclohexanone | 10.04 | 200.00 | 0.510 | Solvent decomposition | |
| Ethyl lactate[1] | 10.01 | 200.03 | 0.500 | 100 | 16 |
| Di(propyleneglycol dimethyl ether) (Proglyde) | 10.04 | 200.05 | 0.502 | 100 | 39 |
| N,N-Dimethyl-acetamide | 10.01 | 200.05 | 0.509 | 17 | 43 |
| N,N-Dimethyl-formamide | 10.01 | 200.05 | 0.501 | Solvent decomposition was observed | |
| o-Dichlorobenzene | 10.02 | 200.06 | 0.500 | 100 | Low[6] |
| Tetraglyme | 10.03 | 200.06 | 0.505 | Solvent decomposition was observed | |
| 1,3-Propanediol | 10.01 | 200.05 | 0.510 | 100 | 0 |
| Water | 10.01 | 200.03 | 0.501 | Decomposition was observed | |
| Dodecane | 2.55 | 50.00 | 0.125 | 97.56 | 85.92 |
| Hexadecane | 2.50 | 50.00 | 0.125 | 99.0 | 82.9 |
| Decane[3] | 30.00 | 60.00 | 0.100 | 81.62 | 97.43 |
| n-Heptane[2,3] | 30.01 | 60.01 | 0.100 | 38.77 | 99.43 |
| Mesitylene[3] | 30.01 | 60.02 | 0.110 | 94.35 | 92.06 |
| p-Xylene[3] | 30.07 | 60.01 | 0.150 | 96.80 | —[8] |
| Acetonitrile[4,5] | 20.01 | 30.00 | 0.150 | 61.00 | 70.10 |
| 2,5-Dimethylfuran | 40.03 | 6.1[7] | 0.503 | 98.92 | 96.12 |
| 2,5-Dimethylfuran | 40.01 | 0 | 0.513 | 95.8 | —[8] |

[1]Pressure increased drastically from 1600 to 2000 psig (at 250° C.) in about 15 minutes, and heating was stopped heating
[2]Reaction temperature = 200° C.
[3]0.1 g dioxane was used as internal standard for GC-MS analysis
[4]Initial pressure of C$_2$H$_4$ = 400 psig instead of 500 psig
[5]Solvent hydrolysis and an increased amount of n-propyltoluene as by-product were observed.
[6]Product not identified by $^1$H-NMR.
[7]Dioxane (6.1 g) was used as solvent.
[8]Selectivity could not be determined.

Example 17

Optimization of DMF and Catalyst Concentrations

This example demonstrates the effect of various concentrations of DMF and Cu(OTf)$_2$ (as the catalyst) in converting DMF into PX. Dodecane alone or a mixture of dodecane and dioxane was used as the solvent. The protocol described in Example 16 was used in for each reagent along with the reaction conditions as summarized in Table 20 below. PX conversion and selectivity for each reaction is also provided in Table 20 below.

TABLE 20

Summary of data

| DMF (g) | Dodecane (g) | Dioxane (g) | Cu(OTf)$_2$ (g) | DMF (%) | Cu(OTf)$_2$ (%) | $g_{DMF}/g_{Cu(OTf)2}$ | Conv. (% mol) | Select. (% mol) |
|---|---|---|---|---|---|---|---|---|
| 2.5 | 50.0 | 0 | 0.125 | 4.75 | 0.24 | 20 | 97.56 | 85.92 |
| 2.5 | 20.4 | 25 | 0.125 | 5.20 | 0.26 | 20 | 97.10 | — |
| 2.5 | 45 | 5 | 0.125 | 4.75 | 0.26 | 20 | 99.39 | 92.17 |
| 20 | 27 | 3 | 0.250 | 39.8 | 0.49 | 80 | 96.94 | 94.40 |
| 20 | 30 | 0 | 0.250 | 39.8 | 0.49 | 80 | 97.77 | 98.73 |
| 20 | 30 | 0 | 0.250 | 39.8 | 0.49 | 80 | 96.56 | 89.76 |
| 20 | 30 | 0 | 2.510 | 38.1 | 4.78 | 8 | 99.49 | 52.22 |
| 30 | 60 | 0.1 | 0.100 | 33.2 | 0.11 | 300 | 81.62 | 97.43 |
| 30 | 60 | 0.1 | 0.100 | 33.2 | 0.11 | 300 | 93.83 | 93.28 |
| 30 | 60 | 0.1 | 0.201 | 33.2 | 0.22 | 150 | 94.26 | 93.03 |

Example 18

Comparison of Mixture of Solvents

This example demonstrates the effect of a mixture of solvents in converting DMF into PX. The solvents used in this Example include para-xylene, dodecane and dioxane. The protocol described in Example 16 was used in for each reagent along with the reaction conditions as summarized in Table 21 below. PX conversion and selectivity for each reaction is also provided in Table 21 below.

TABLE 21

Summary of solvent mixture data

| DMF (g) | PX (as solvent) (g) | Dodecane (g) | Dioxane (g) | Cu(OTf)$_2$ (g) | Conversion (g) | Selectivity (g) |
|---|---|---|---|---|---|---|
| 30.07 | 60.01 | 0 | 0.100 | 0.150 | 96.80 | 0 |
| 30.82 | 45.01 | 15.00 | 0 | 0.150 | 95.52 | 74.90 |
| 30.03 | 45.03 | 15.26 | 0 | 0.150 | 95.29 | 81.84 |
| 12.97 | 45.02 | 5.00 | 0 | 0.150 | 98.81 | 78.93 |
| 30.00 | 30.01 | 30.00 | 0 | 0.150 | 95.20 | 84.30 |
| 30.00 | 30.00 | 30.02 | 0 | 0.150 | 94.50 | 81.90 |
| 30.00 | 60.00 | 0 | 0.220 | 0.209* | 6.50 | — |

*Copper(II) acetate instead of copper(II) triflate

Example 19

Comparison of Catalysts

This example compares the effect of various catalysts in converting DMF into PX. The protocol described in Example 16 was used in for each catalyst and solvent along with the reaction conditions as summarized in Table 22 below. PX conversion and selectivity for each reaction is also provided in Table 22 below.

TABLE 22

Summary of catalyst data

| Catalyst | Amount Cat. (g) | Solvent | Amount Solv. (g) | DMF (g) | Conv. (%) | Select. (%) |
|---|---|---|---|---|---|---|
| La(OTf)$_3$ | 0.500 | Dioxane | 200.04 | 10.01 | 100 | 83.5 |
| Nd(OTf)$_3$ | 0.500 | Dioxane | 200.01 | 10.01 | 100 | 90.4 |
| Sc(OTf)$_3$ | 0.500 | Dioxane | 200.05 | 10.04 | 99.1 | 87.0 |
| Cu[N(Tf)$_2$]$_2$ | 0.500 | Dioxane | 200.02 | 10.01 | 98.6 | 95.8 |
| Y(OTf)$_3$ | 0.125 | Dodecane[1] | 45.00 | 2.50 | 99.9 | 94.5 |
|  | 0.500 | Triglyme | 200.00 | 10.00 | 99.0 | 82.0 |
| CuCl$_2$ × 2H$_2$O | 0.500 | Dioxane | 200.00 | 10.06 | 81.5 | 91.5 |
| CuCl$_2$ anhydrous | 1.500 | Triglyme | 170.00 | 30.00 | 50.4 | 91.8 |
| H$_4$[SiMo$_{12}$O$_{40}$] × H$_2$O | 0.510 | Dioxane | 200.05 | 10.00 | 98.8 | 84.2 |
|  | 0.250 | Triglyme | 100.00 | 5.00 | — | — |
| H$_3$[PMo$_{12}$O$_{40}$] × H$_2$O | 0.510 | Dioxane | 200.07 | 10.04 | 97.9 | 78.0 |
| Cu(OCOCH$_3$)$_2$ | 0.125 | Dioxane | 50.00 | 2.50 | 86.2 | 112 |
|  | 0.150 | Dodecane[2] | 30.00 | 20.00 | 5.3 | 43.1 |
|  | 0.209 | p-Xylene[3] | 60.00 | 30.00 | 6.57 | −63.8 |
|  | 0.150 | Triglyme | 30.00 | 20.03 | 13.5 | 40.6 |
| Cu(CH$_3$COCH$_2$COCH$_3$)$_2$ | 0.125 | Dioxane | 50.00 | 2.50 | 80.2 | 93.6 |
|  | 0.150 | Dodecane[2] | 30.01 | 20.02 | 2.5 | 52.7 |
|  | 0.150 | Triglyme | 30.00 | 20.03 | 12.8 | 8.0 |
| Cu(II)(BF$_4$)$_2$ | 0.125 | Dioxane | 50.01 | 2.50 | 80.01 | 100.02 |
| Cu(I)(BF$_4$)(CH$_3$CN)$_4$ | 0.133 | Dodecane | 30.02 | 20.02 | 11.6 | 22.7 |
| Cu(I)(BF$_4$)(CH$_3$CN)$_4$-in situ from Cu$_2$O + HBF$_4$ + CH$_3$CN | 0.131 | Dodecane | 30.01 | 20.01 | 8.8 | 50.7 |
|  | 0.131 | Dodecane | 30.00 | 20.00 | 53.1 | 58.8 |
|  | 0.131 | Dodecane | 30.00 | 20.00 | 58.1 | 59.5 |
| [Cu(I)OTf]$_2$C$_6$H$_6$ | 0.209 | Dodecane | 30.00 | 20.04 | 94.1 | 97.6 |
| (Cu(I)OTf)(CH$_3$CN)$_4$ | 0.152 | Dodecane | 30.02 | 20.01 | 58.7 | 85.0 |
| (Cu(I)OSO$_2$CF$_3$)(CH$_3$CN)$_4$-in situ | 0.391 | Dodecane | 75.03 | 50.00 | 80.2 | 73.5 |

TABLE 22-continued

Summary of catalyst data

| Catalyst | Amount Cat. (g) | Solvent | Amount Solv. (g) | DMF (g) | Conv. (%) | Select. (%) |
|---|---|---|---|---|---|---|
| from $Cu_2O$ + $CF_3SO_3H$ + $CH_3CN$ | 0.391 | Dodecane | 75.00 | 50.00 | 79.6 | 77.9 |
|  | 0.156 | Dodecane | 30.00 | 20.02 | 96.2 | 74.0 |
| $CF_3SO_3H$ | 0.130 | Dodecane | 30.00 | 20.00 | 92.1 | 86.0 |
|  | 0.325 | Dodecane | 75.03 | 50.02 | 94.9 | 87.6 |
| Copper (45 micron) | 0.030 | Dodecane | 30.03 | 20.00 | 10.3 | 4.7 |
| Nafion NR50 | 0.533 | Dodecane | 30.00 | 20.00 | 69.5 | 74.3 |

[1] 5.01 g dioxane used in the mixture with dodecane;
[2] 0.1 g of dioxane was used as internal standard;
[3] 0.22 g of dioxane was used as internal standard;
[4] 400 psig $C_2H_4$ instead of 500 psig;
[5] $HBF_4$ was used in excess (3.69/1);
[6] $CF_3SO_3H$ was used in excess (1.7/1)

Based on the results in Table 22 above, DMF was observed to convert into PX in the presence of triflate catalysts with conversions of at least 98% and selectivity of at least 84% in either dioxane or dodecane. Heteropolyacids such as 12-Molybdosilicic acid monohydrate and 12-Molybdophosphoric acid monohydrate were observed to convert PX with conversions of about 98% and selectivity of about 80% when dioxane was used as solvent. Additionally, it was surprisingly observed that triflic acid alone catalyzed the conversion of DMF into PX.

Example 20

Comparison of Ethylene Pressure

This example compares the effect of varying the ethylene pressure in converting DMF into PX. The protocol described in Example 16 was used for ethylene pressures as summarized in Table 23 (ethylene pressure around the supercritical point) and Table 24 (ethylene pressure below 500 psig). Supercritical ethylene point is about 50 bar (725 psi) at 10° C. At 250° C., the supercritical pressure is about 725 psi (739.7 psig). For each ethylene pressure specified in Table 23 below, two experiments (with and without stirring) were performed to also assess the effect of the mixing on the reaction. PX conversion and selectivity for each reaction is also provided in Tables 23 and 24 below.

TABLE 23

Summary of data for ethylene pressure around the supercritical point (initial composition of reaction mixture: 30.0 g dodecane + 20.0 g DMF, 0.15 g $Cu(OTf)_2$ + 0.10 g dioxane)

| Regime | Initial $P_{C2H2}$ at 250° C. (psig) | Pressure var., (psig) (Temp. var., (° C.)) | Conversion (%) | Selectivity (%) |
|---|---|---|---|---|
| sub-supercritical with mixing | 650 | 625-700 (246-252) | 87.37 | 95.36 |
| sub-supercritical without mixing | 650 | 600-700 (240-258) | 89.65 | 82.82 |
| above supercritical with mixing | 800 | 750-800 (246-252) | 88.99 | 95.80 |
| above supercritical without mixing | 800 | 240-260 (750-825) | 93.01 | 86.84 |

TABLE 24

Summary of data for ethylene pressure below 500 psig (initial composition of reaction mixture: 30.0 g dodecane + 20.0 g DMF, 0.15 g $Cu(OTf)_2$ + 0.10 g dioxane)

| $P_{C2H4}$, initial (psig) | $P_{C2H4}$ after refill* (psig) | p@250° C. (psig) | p(@° C.) after exp. (psig) | Amount $C_2H_4$ (g)(calc) | Molar ratio $C_2H_4$/DMF (calc) | Conv. (%) | Select. (%) |
|---|---|---|---|---|---|---|---|
| 100 | 110 | 225-300 | <100 (26) | 3.21 | 0.6 | 49.14 | 81.6 |
| 150 | 190 | 300-375 | 100 (26) | 5.27 | 0.9 | 62.7 | 84.0 |
| 200 | 250 | 400-500 | 160 (26) | 6.81 | 1.2 | 74.21 | 89.43 |
| 250 | 300 | 500-600 | 175 (25) | 8.10 | 1.4 | 78.03 | 95.33 |
| 300 | 375 | 675-850 | 250 (25) | 10.03 | 1.7 | 88.11 | 93.74 |
| 350 | 425 | 825-900 | 250 (8) | 11.32 | 1.9 | 91.88 | 86.40 |
| 400 | 500 | 1000-1100 | 325 (25) | 13.25 | 2.3 | 93.21 | 96.28 |

*$P_{C2H4\ after\ refill}$ = total ethylene charged in the Parr reactor which takes into account the initial pressure charged and the refill needed to bring the pressure back to the initial pressure after it dropped as a consequence of ethylene dissolution in the reaction mixture with mixing. For instance, when 100 psig ethylene were charged initially, the pressure dropped with mixing to 90 psig. The pressure was re-adjusted to the initial pressure by adding 10 psig (refill), therefore the total pressure charged was 110 psig.

Example 21

Comparison of Catalysts in Reaction with SolTrol

Soltrol 170 (30 g), 2,5-dimethylfuran (20 g, 0.208 mol) and the catalyst specified in Table 25 below were charged in the Parr vessel. The reactor was sealed, placed in the heating mantle and attached to the nitrogen line, ethylene cylinder, temperature controller and a waste container (through the gas release valve). The reaction mixture was flushed three times with nitrogen (nitrogen pressure ≅80 psig) and three times with ethylene (ethylene pressure ≅100 psig) then 500 psig ethylene was introduced in the reaction mixture and the mixture stirred at 1020-1025 Hz. The ethylene pressure dropped with stirring to 357 psi. The pressure was readjusted to 500 psig by adding more ethylene, so that the total ethylene introduced was 655 psi. The reaction mixture was heated to 250° C. and maintained at this temperature for 7 hours. At the end of the reaction time, the heating mantle was removed and the exterior of the Parr reactor was subjected to a nitrogen flow to enable cooling. Once the reactor was brought to room temperature the excess ethylene was slowly released through the gas release valve and the reaction mixture was transferred into a sample container and submitted to analysis by NMR and GC-MS.

TABLE 25

Summary of data

| Catalyst | Catalyst | Soltrol 170 | DMF | Conv. (%) | Select. (%) |
|---|---|---|---|---|---|
| p-Toluene sulfonic acid monohydrate | 0.0805 g 0.424 mmol pTSA$x$H$_2$O | 30.02 | 20.00 | 29.7 | 67.4 |
| H$_2$SO$_4$ ACS grade, 95-98% | 0.110 g solution 95% 1.037 mmol H$_2$SO$_4$ | 75.01 | 50.02 | 12.4 | 6.8 |
| HCl 1M sol. in diethyl ether | 0.303 g solution HCl in diethyl ether 0.415 mmol HCl | 30.02 | 20.01 | 19.6 | 35.2 |
| HBF$_4$ 48% aqueous sol. | 0.2019 g HBF$_4$ 48% aqueous sol. 1.10 mmol HBF$_4$ | 75.03 | 50.04 | 17.6 | 28.2 |
| Methane sulfonic acid | 0.085 g 0.884 mmol | 75.02 | 50.00 | 18.1 | 45.2 |
| H$_3$PO$_4$ 85% | 0.1280 g solution 1.11 mmol | 30.00 | 20.02 | 13.2 | 31.7 |

Example 22

Comparison of Solvents in Reaction with Triflic Acid

The solvent specified in Table 26 below, 2,5-dimethylfuran and triflic acid were charged in the Parr vessel and the reactor was sealed, placed in the heating mantle and attached to the nitrogen line, ethylene cylinder, temperature controller and a waste container (through the gas release valve). The reaction mixture was flushed three times with nitrogen (nitrogen pressure ≅80 psig) and three times with ethylene (ethylene pressure ≅100 psig) then 500 psig ethylene was introduced in the reaction mixture and the mixture stirred at 1020-1025 Hz. The ethylene pressure dropped with stirring to a certain value (depending on the solvent used) where it stabilized. The pressure was readjusted to 500 psig by adding more ethylene, so that the total ethylene introduced was 655 psi. The reaction mixture was heated to 250° C. and maintained at this temperature for 7 hours. At the end of the reaction time, the heating mantle was removed and the exterior of the Parr reactor was subjected to a nitrogen flow to enable cooling. Once the reactor was brought to room temperature the excess ethylene was slowly released through the gas release valve and the reaction mixture was transferred into a sample container and submitted to analysis by NMR and GC-MS.

TABLE 26

Summary of data

| | | Amount [g] | |
|---|---|---|---|
| Solvent | Solvent | 2,5-Dimethylfuran | Triflic acid |
| Soltrol 130 | 30.00 | 20.01 | 0.1307 (0.87 mmol) |
| Soltrol 170 | 30.02 | 20.02 | 0.1316 (0.88 mmol) |
| Soltrol 220 | 30.03 | 20.00 | 0.1342 (0.89 mmol) |
| Dioxane | 75.01 | 50.01 | 0.4076 (2.72 mmol) |
| p-Xylene | 75.01 | 50.01 | 0.3479 (2.32 mmol) |

Example 23

Effect of n-Heptane and Dodecane as Solvents and Zeolite as Catalyst n-Heptane (52.3 g), dodecane (7.82 g), 2,5-dimethylfuran (11.54 g, 0.120 mol) (1.2 M solution of 2,5-dimethylfuran in the mixture of n-heptane and dodecane) and 0.45 g calcined β-zeolite (Zeolyst CP 814 E) were charged in the Parr vessel and the reactor was sealed, placed in the heating mantle and attached to the nitrogen line, ethylene cylinder, temperature controller and a waste container (through the gas release valve). The reaction mixture was flushed three times with nitrogen (nitrogen pressure ≅80 psig) and three times with ethylene (ethylene pressure ≅100 psig) then 200 psig ethylene was introduced in the reaction mixture under stirring at 1020 Hz. The reaction mixture was heated to 250° C. and maintained at this temperature for 24 hours. At the end of the reaction time, the heating mantle was removed and the exterior of the Parr reactor was subjected to a nitrogen flow to enable cooling. Once the reactor was brought to room temperature the excess ethylene was slowly released through the gas release valve.

TABLE 27

Summary of data

| Exp. | DMF [g] | n-Heptane [g] | Dodecane [g] | Zeolyst CP 814E* [g] | Conv. [%] | Select. [%] |
|---|---|---|---|---|---|---|
| 1 | 11.54 | 52.30 | 7.82 | 0.45 | 76 | 59 |
| 2 | 11.54 | 52.30 | 7.82 | 0.45 | 94 | 89 |

*The catalyst used in the two experiments was obtained in two different batches.

What is claimed:

1. A method for producing one or more compounds of formula I:

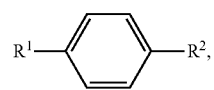

(I)

wherein each $R^1$ and $R^2$ is independently hydrogen or alkyl, the method comprising:
  combining one or more compounds of formula A:

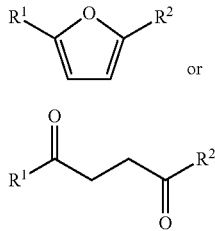
  (A)

or

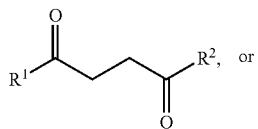
  (B)

one or more compounds of formula B:

(B)

any combination of one or more compounds of formula A and one or more compounds of formula B, wherein $R^1$ and $R^2$ in formulae A and B are as defined in formula I above, with
  (i) ethylene, and
  (ii) a sulfonic acid, or an ester, anhydride or resin thereof, or
  a sulfonimide or a sulfonimide salt,
to produce one or more compounds of formula I from at least a portion of the one or more compounds of formula A, the one or more compounds of formula B, or any combinations thereof, and at least a portion of the ethylene.

2. The method of claim 1, wherein each $R^1$ and $R^2$ is independently alkyl; or $R^1$ is alkyl and $R^2$ is hydrogen.

3. The method of claim 1, wherein:
the sulfonic acid has a structure of formula $R^xSO_3H$;
wherein $R^x$ is alkyl, haloalkyl, cycloalkyl, heterocycloalkyl, aryl, or heteroaryl,
  wherein each alkyl, haloalkyl, cycloalkyl, heterocycloalkyl, aryl, or heteroaryl is optionally substituted with 1 to 8 substituents independently selected from the group consisting of alkyl, haloalkyl, cycloalkyl, heterocycloalkyl, aryl, heteroaryl, nitro, —OR', —C(O)OR', —C(O)NR'R", —CHO, —COR', and cyano,
  wherein each R' and R" is independently hydrogen, alkyl, or haloalkyl.

4. The method of claim 1, wherein:
the sulfonimide has a structure of formula $(R^{y1}SO_2)NH(SO_2R^{y2})$; and
the sulfonimide salt has a structure of formula $Q^{r+}[(R^{y1}SO_2)N(R^{y2}SO_2)]_r$,
wherein each $R^{y1}$ and $R^{y2}$ is independently alkyl, haloalkyl, cycloalkyl, heterocycloalkyl, aryl, or heteroaryl,
  wherein each alkyl, haloalkyl, cycloalkyl, heterocycloalkyl, aryl, or heteroaryl is optionally substituted with 1 to 8 substituents independently selected from the group consisting of alkyl, haloalkyl, cycloalkyl, heterocycloalkyl, aryl, heteroaryl, nitro, —OR', —C(O)OR', —C(O)NR'R", —CHO, —COR', and cyano,
  wherein each R' and R" is independently hydrogen, alkyl, or haloalkyl,
Q (if present) is a cation; and
r (if present) is the charge of the cation.

5. The method of claim 4, wherein $Q^{r+}$ is $Al^{3+}$, $Bi^{3+}$, $Cu^{2+}$, $Cu^+$, $Cr^{3+}$, $Fe^{3+}$, $Gd^{3+}$, $In^{3+}$, $Ni^{2+}$, $Nd^{3+}$, $Li^+$, $Na^+$, $K^+$, $Rb^+$, $Cs^+$, $Mg^{2+}$, $Ba^{2+}$, $Ca^{2+}$, $La^{3+}$, $Sc^{3+}$, $Ti^{4+}$, $V^{5+}$, $Y^{3+}$, $Zn^{2+}$, $Pt^{2+}$, $Pd^{2+}$, $Ag^+$, $Au^{3+}$, $Tl^{3+}$, $Tl^+$, $Re^{3+}$, $Hg_2^{2+}$, $Hg^{2+}$, $NH_4^+$, $Sn^{4+}$, $Sn^{3+}$, $Sn^{2+}$, $B^{3+}$, $Ga^{3+}$, $Pb^{4+}$, $Pb^{2+}$, $CO^{3+}$, $CO^{2+}$, $Ge^{4+}$, $Ge^{2+}$, $Ce^{4+}$, or $Ce^{3+}$.

6. The method of claim 1, wherein the sulfonic acid or resin thereof, or the sulfonimide or the sulfonimide salt is $CF_3SO_3H$, $HCF_2CF_2SO_3H$, $C_6F_5SO_3H$, 4-methylbenzenesulfonic acid, 2,4-dinitrobenzenesulfonic acid, $NH(Tf)_2$, $Al[N(Tf)_2]_3$, $Bi[N(Tf)_2]_3$, $Cu[N(Tf)_2]_2$, $Cu[N(Tf)_2]$, $Cr[N(Tf)_2]_3$, $Fe[N(Tf)_2]_3$, $Gd[N(Tf)_2]_3$, $In[N(Tf)_2]_3$, $Ni[N(Tf)_2]_2$, $Nd[N(Tf)_2]_3$, $Li[N(Tf)_2]$, $Na[N(Tf)_2]$, $K[N(Tf)_2]$, $Rb[N(Tf)_2]$, $Cs[N(Tf)_2]$, $Mg[N(Tf)_2]_2$, $Ba[N(Tf)_2]_2$, $Ca[N(Tf)_2]_2$, $La[N(Tf)_2]_3$, $Sc[N(Tf)_2]_3$, $Ti[N(Tf)_2]_4$, $V[N(Tf)_2]_5$, $Y[N(Tf)_2]_3$, $Zn[N(Tf)_2]_2$, $Pt[N(Tf)_2]_2$, $Pd[N(Tf)_2]_2$, $Ag[N(Tf)_2]$, $Ag[N(Tf)_2]_2$, $Au[N(Tf)_2]_3$, $Tl[N(Tf)_2]_3$, $Tl[N(Tf)_2]$, $Re[N(Tf)_2]_3$, $Hg_2[N(Tf)_2]_2$, $Hg[N(Tf)_2]_2$, $NH_4[N(Tf)_2]$, $Sn[N(Tf)_2]_4$, $Sn[N(Tf)_2]_3$, $Sn[N(Tf)_2]_2$, $B[N(Tf)_2]_3$, $Ga[N(Tf)_2]_3$, $Pb[N(Tf)_2]_4$, $Pb[N(Tf)_2]_2$, $Co[N(Tf)_2]_3$, $Co[N(Tf)_2]_2$, $Ge[N(Tf)_2]_4$, $Ge[N(Tf)_2]_3$, $Ge[N(Tf)_2]_2$, $Ge[N(Tf)_2]$, $Ce[N(Tf)_2]_4$, $Ce[N(Tf)_2]_3$, ethyldimethylpropylammonium bis(trifluoromethylsulfonyl)imide, 1-butyl-1-methylpyrrolidinium bis(trifluoromethylsulfonyl)imide, 1-ethyl-3-methylimidazolium bis(trifluoromethylsulfonyl)imide, 1-butyl-3-methylimidazolium bis(trifluoromethylsulfonyl)imide, 1-allyl-3-methylimidazolium bis(trifluoromethylsulfonyl)imide, triethylsulfonium bis(trifluoromethylsulfonyl)imide, 1,2-dimethyl-3-propylimidazolium bis(trifluoromethylsulfonyl)imide, $[(C_6H_{13})_3(C_{14}H_{29})P]^+[(CF_3SO_2)_2N]^-$, $[C_{11}H_{16}N]^+[N(SO_2CF_3)_2]^-$, $[C_8H_{15}N_2]^+[N(SO_2CF_3)_2]^-$, $[C_6H_{11}N_2]^+[N(SO_2CF_2CF_3)_2]^-$, $[C_6H_{11}N_2]^+[N(SO_2CF_3)_2]^-$, or $[C_6H_{14}N]^+[N(SO_2CF_3)_2]^-$, or any combinations thereof.

7. The method of claim 1, wherein $R^1$ and $R^2$ are each alkyl.

8. The method of claim 7, wherein $R^1$ and $R^2$ are each methyl.

9. The method of claim 1, further comprising combining a solvent system with the compound of formula A, the compound of formula B, or any combination thereof, the ethylene, and the sulfonic acid, or an ester, anhydride or resin thereof, or the sulfonimide or the sulfonimide salt.

10. The method of claim 9, wherein the solvent system comprises an alkyl phenyl solvent, an ether solvent, an ester solvent, an alcohol solvent, a ketone solvent, an ionic liquid, or any combinations or mixtures thereof.

11. The method of claim 9, wherein the solvent system comprises dimethylacetamide, acetonitrile, sulfolane, dioxane, dimethyl ether, diethyl ether, glycol dimethyl ether, ethylene glycol diethyl ether, diethylene glycol dimethyl ether, diethylene glycol diethyl ether, triethylene glycol dimethyl ether, diethylene glycol dibutyl ether, tetraethylene glycol dimethyl ether, polyglyme, proglyme, higlyme, tetrahydrofuran, ethylene glycol, diethylene glycol, triethylene glycol, polyethylene glycol, cyclobutanone, cyclopentanone, cyclohexanone, cycloheptanone, cyclooctanone, methyl acetate, ethyl acetate, propyl acetate, butyl acetate, methyl lactate, ethyl lactate, propyl lactate, butyl lactate, triacetin, dibutylphthalate, butane, pentane, cyclopentane, hexane, cyclohexane, heptane, cycloheptane, octane, cyclooctane, nonane, decane, undecane, dodecane, hexadecane, tetrachloride, chloroform, dichloromethane, nitromethane, toluene, anisole, nitrobenzene, bromobenzene, methylpyrrole, methylpyrrolidone, dimethylfuran, dichlorobenzene, para-xylene, mesitylene, dodecylbenzene, pentylbenzene, hexylbenzene, diphenyl ether, methyldiphenyl ether, ethyldiphenyl ether, water, or any combinations or mixtures thereof.

12. The method of claim 1, wherein:
$R^1$ and $R^2$ are each methyl; and
the one or more compounds of formula A, one or more compounds of formula B, or any combinations thereof, and the ethylene are combined with a sulfonic acid or a resin thereof.

13. The method of claim 12, wherein:
the sulfonic acid is triflic acid.

14. The method of claim 13, wherein the solvent system comprises para-xylene.

15. The method claim 1, wherein the sulfonimide salt comprises a metal.

16. The method of claim 1, wherein the sulfonic acid or resin thereof, or the sulfonimide or the sulfonimide salt is produced in situ.

17. The method of claim 9, wherein the solvent system comprises aliphatic solvent.

18. The method of claim 9, wherein the solvent system comprises aromatic solvent.

19. The method of claim 9, wherein the solvent system comprises alkyl phenyl solvent.

20. The method of claim 13, wherein the solvent system comprises C4-C30 alkyl solvent.

21. The method of claim 1, wherein the one or more compounds of formula A, the one or more compounds of formula B, or any combinations thereof, and the ethylene are combined with a sulfonic acid.

22. The method of claim 1, wherein the one or more compounds of formula A, the one or more compounds of formula B, or any combinations thereof, and the ethylene are combined with a sulfonic acid resin.

23. The method of claim 1, wherein the one or more compounds of formula A, the one or more compounds of formula B, or any combinations thereof, and the ethylene are combined with a sulfonimide or a sulfonimide salt.

24. The method of claim 3, wherein:
$R^x$ is alkyl, haloalkyl, cycloalkyl, or aryl,
wherein each alkyl, haloalkyl, cycloalkyl, or aryl is optionally substituted with 1 to 8 substituents independently selected from the group consisting of alkyl, haloalkyl, cycloalkyl and aryl.

25. The method of claim 4, wherein:
each $R^{y1}$ and $R^{y2}$ is independently alkyl, haloalkyl, cycloalkyl, or aryl,
wherein each alkyl, haloalkyl, cycloalkyl, or aryl is optionally substituted with 1 to 8 substituents independently selected from the group consisting of alkyl, haloalkyl, cycloalkyl and aryl.

26. A method for producing one or more compounds of formula I:

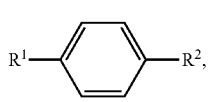
(I)

wherein each $R^1$ and $R^2$ is independently hydrogen or alkyl, the method comprising combining:
one or more compounds of formula A:

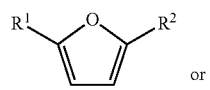
(A)

or

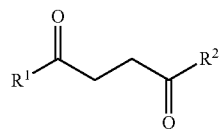
(B)

or one or more compounds of formula B:

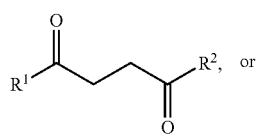
(B)

or any combination of one or more compounds of formula A and one or more compounds of formula B, wherein $R^1$ and $R^2$ in formulae A and B are as defined in formula I above, with
(i) ethylene, and
(ii) $R^{x1}CF_2SO_3H$, wherein $R^{x1}$ is alkyl or haloalkyl, to produce one or more compounds of formula I from at least a portion of the one or more compounds of formula A, the one or more compounds of formula B, or any combinations thereof, and at least a portion of the ethylene.

27. A method for producing one or more compounds of formula I:

(I)

wherein each $R^1$ and $R^2$ is independently hydrogen or alkyl, the method comprising combining:
one or more compounds of formula A:

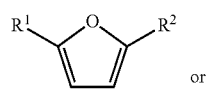
(A)

or

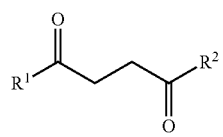
(B)

or one or more compounds of formula B:

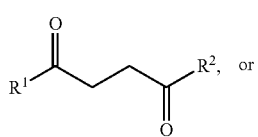

(B)

or any combination of one or more compounds of formula A and one or more compounds of formula B, wherein $R^1$ and $R^2$ in formulae A and B are as defined in formula I above, with:
(i) ethylene, and
(ii) a sulfonamide or a sulfonamide salt, wherein:
the sulfonamide has a structure of formula $(R^{y1}SO_2)NH_2$ or $(R^{y1}SO_2)NH(R^z)$; and
the sulfonamide salt has a structure of formula $Q^{r+}[(R^{y1}SO_2)N(R^z)]_r$ or $Q^{r+}[(R^{y1}SO_2)NH]_r$;
wherein each $R^{y1}$, $R^{y2}$ and $R^z$ is independently alkyl, haloalkyl, cycloalkyl, heterocycloalkyl, aryl, or heteroaryl,
wherein each alkyl, haloalkyl, cycloalkyl, heterocycloalkyl, aryl, or heteroaryl is optionally substituted with 1 to 8 substituents independently selected from the group consisting of alkyl, haloalkyl, cycloalkyl, heterocycloalkyl, aryl, heteroaryl, nitro, —OR', —C(O)OR', —C(O)NR'R''—CHO, —COR', and cyano,
wherein each R' and R'' is independently hydrogen, alkyl, or haloalkyl,
Q (if present) is a cation; and
r (if present) is the charge of the cation,
to produce one or more compounds of formula I from at least a portion of the one or more compounds of formula A, the one or more compounds of formula B, or any combinations thereof, and at least a portion of the ethylene.

28. The method of claim 27, wherein:
each $R^{y1}$, $R^{y2}$ and $R^z$ is independently alkyl, haloalkyl, cycloalkyl, or aryl,
wherein each alkyl, haloalkyl, cycloalkyl, or aryl is optionally substituted with 1 to 8 substituents independently selected from the group consisting of alkyl, haloalkyl, cycloalkyl and aryl.

* * * * *